United States Patent

Lawton et al.

[11] Patent Number: 4,743,687
[45] Date of Patent: May 10, 1988

[54] PYRIDAZO (1,2-A) (1,2) DIAZEPINE DERIVATIVES

[75] Inventors: Geoffrey Lawton, Hitchin; Sally Redshaw, Stevenage, both of England

[73] Assignee: Hoffmann-La Roche Inc., Nutley, N.J.

[21] Appl. No.: 877,085

[22] Filed: Jun. 23, 1986

[30] Foreign Application Priority Data

Jul. 1, 1985 [GB] United Kingdom ............ 8516604
Apr. 18, 1986 [GB] United Kingdom ............ 8609591

[51] Int. Cl.$^4$ ................ C07D 487/04; C07D 237/04; A61K 31/50; A61K 31/55
[52] U.S. Cl. ..................... 540/487; 540/500; 544/61; 544/116; 544/232; 544/235; 544/236; 544/224; 514/221
[58] Field of Search ............................ 540/487, 500

[56] References Cited

U.S. PATENT DOCUMENTS

| | | | |
|---|---|---|---|
| 4,307,094 | 12/1981 | Hassall et al. | 544/236 |
| 4,341,781 | 7/1982 | Hassall et al. | 544/235 |
| 4,399,136 | 8/1983 | Hassall et al. | 544/235 |
| 4,512,924 | 4/1985 | Atwood et al. | 540/487 |
| 4,692,438 | 9/1982 | Hassall et al. | 514/183 |

*Primary Examiner*—Robert T. Bond
*Attorney, Agent, or Firm*—Jon S. Saxe; Bernard S. Leon; George W. Johnston

[57] ABSTRACT

Compounds of the formula

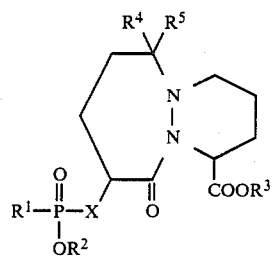

wherein $R^1$ represents hydroxy, alkyl, aralkyl, aralkoxy-alkyl, hydroxy-alkyl, amino-alkyl, acylamino-alkyl, monoalkylamino-alkyl, dialkylamino-alkyl, alkoxycarbonylamino-alkyl, halo-alkyl, carboxy-alkyl, alkoxycarbonyl-alkyl, alkoxy or aralkoxy; $R^2$ and $R^3$ each represent hydrogen, alkyl or aralkyl; $R^4$ and $R^5$ each represent hydrogen or $R^4$ and $R^5$ together represent oxo; and X represents an oxygen atom or the group $-NR^6-$ in which $R^6$ represents hydrogen, alkyl or aralkyl or $-(CH_2)_n-$ in which n stands for zero, 1 or 2, and racemates, enantiomers, diastereoisomers or pharmaceutically acceptable salts thereof have antihypertensive activity and can be used as medicaments in the form of pharmaceutical preparations. They can be prepared according to known methods.

Compounds useful as starting materials for producing the compounds of formula I are also provided.

21 Claims, No Drawings

PYRIDAZO (1,2-A) (1,2) DIAZEPINE DERIVATIVES

FIELD OF THE INVENTION

The present invention is concerned with pyridazo[1,2-a][1,2]diazepine derivatives, a process for the manufacture thereof and medicaments containing said derivatives.

SUMMARY OF THE INVENTION

The present invention provides pyridazo[1,2-a][1,2]diazepine derivatives of the formula

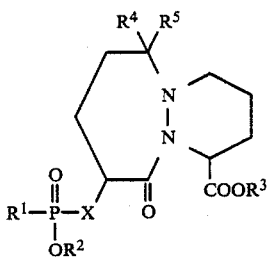

I wherein $R^1$ represents hydroxy, alkyl, aralkyl, aralkoxy-alkyl, hydroxy-alkyl, amino-alkyl, acylamino-alkyl, monoalkylamino-alkyl, dialkylamino-alkyl, alkoxycarbonylamino-alkyl, halo-alkyl, carboxy-alkyl, alkoxycarbonyl-alkyl, alkoxy or aralkoxy; $R^2$ and $R^3$ each represent hydrogen, alkyl or aralkyl; $R^4$ and $R^5$ each represent hydrogen or $R^4$ and $R^5$ together represent oxo; and X represents an oxygen atom or the group —$NR^6$— in which $R^6$ represents hydrogen, alkyl or aralkyl or —$(CH_2)_n$— in which n stands for zero, 1 or 2, and racemates, enantiomers, diastereoisomers or pharmaceutically acceptable salts thereof.

The compounds of formula I and their aforementioned pharmaceutically acceptable salts are useful as antihypertensive agents. They inhibit the activity of angiotensin converting enzyme (ACE), which enzyme would otherwise bring about the undesirable conversion of angiotensin I into angiotensin II. The compounds are therefore useful in reducing or alleviating angiotensin-related hypertension. Accordingly, the compounds are useful, inter alia, in the treatment of high blood pressure.

As starting materials useful for producing certain of the compounds within the scope of formula I, the present invention also provides compounds of the formula

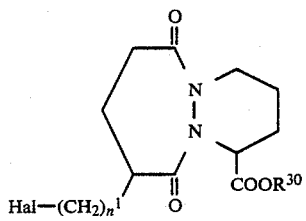

IIa wherein $R^{30}$ represents alkyl or aralkyl, Hal represents a halogen atom and $n^1$ stands for 1 or 2; and compounds of the formula

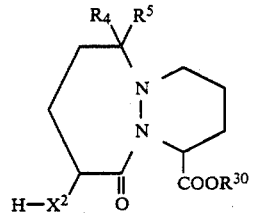

IVa wherein $R^4$ and $R^5$ each represent hydrogen or $R^4$ and $R^5$ together represent oxo; $R^{30}$ represents alkyl or aralkyl; and $X^2$ represents an oxygen atom or the group —$NR^{61}$— in which $R^{61}$ represents alkyl or aralkyl, and racemates enantiomers or diastereomers of these compounds of formulae IIa and IVa.

DETAILED DESCRIPTION OF THE INVENTION

The pyridazo[1,2-a][1,2]diazepine derivatives provided by the present invention are compounds of the formula

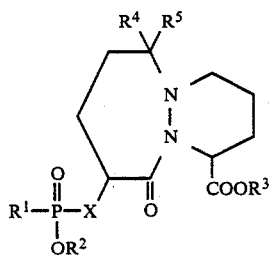

I wherein $R^1$ represents hydroxy, alkyl, aralkyl, aralkoxy-alkyl, hydroxy-alkyl, amino-alkyl, acylamino-alkyl, monoalkylamino-alkyl, dialkylamino-alkyl, alkoxycarbonylamino-alkyl, halo-alkyl, carboxy-alkyl, alkoxycarbonyl-alkyl, alkoxy or aralkoxy; $R^2$ and $R^3$ each represent hydrogen, alkyl or aralkyl; $R^4$ and $R^5$ each represent hydrogen or $R^4$ and $R^5$ together represent oxo; and X represents an oxygen atom or the group —$NR^6$— in which $R^6$ represents hydrogen, alkyl or aralkyl or —$(CH_2)_n$— in which n stands for zero, 1 or 2, and pharmaceutically acceptable salts thereof.

Unless otherwise indicated, the formulae in the specification are shown as racemates. The compounds of formula I contain two asymmetric carbon atoms and, when $R^1$ and $OR^2$ have different significances, a chiral phosphorus atom. Accordingly, the present invention, including the pictorial representations of the inventive compounds, include optically active enantiomers and diastereoisomers as well as racemates.

As used in this specification, the term "alkyl", alone or in combination, means a straight-chain or branched-chain alkyl group which contains from 1 to 8, preferably from 1 to 4, carbon atoms (e.g. methyl, ethyl, propyl, isopropyl, butyl, tert.butyl, pentyl, hexyl etc). The term "aralkyl" means an alkyl group as defined above in which a hydrogen atom has been replaced by a phenyl group or a phenyl group substituted with one or more substituents selected from halogen, alkyl, alkoxy, trifluoromethyl, nitro, amino, iminoalkylamino etc., examples of aralkyl groups being benzyl, phenethyl, 3-phenylpropyl, 4-chlorobenzyl, 4-methoxybenzyl, 3-(4-chlorophenyl)propyl, 3-(4-methoxy-phenyl)propyl, 4- nitrophenethyl, 4-aminophenethyl, 4-(1-iminoethylamino)phenethyl etc.

The term "halogen" used herein means fluorine, chlorine, bromine or iodine.

The term "hydroxy-alkyl" means an alkyl group substituted with a hydroxy moiety. Examples of hydroxy-alkyl groups are hydroxymethyl, 2-hydroxyethyl etc.

The term "amino-alkyl" means an alkyl group substituted with an amino moiety. The amino-alkyl group can be, for example, aminomethyl, 2-aminoethyl etc. Methylaminomethyl, 2-methylaminoethyl and 2-ethylaminoethyl are examples of monoalkylamino-alkyl groups and 2-dimethylaminoethyl, 2-diethylaminoethyl and 3-dimethylaminopropyl are examples of dialkylamino-alkyl groups. The term "acyl" as used in the term "acylaminoalkyl" connotes a radical derived, for example, from a saturated or unsaturated aliphatic carboxylic acid, from a cycloaliphatic carboxylic acid, from an aromatic carboxylic acid, from an araliphatic carboxylic acid or from a heterocyclic carboxylic acid, examples of such acids being acetic acid, propionic acid, butyric acid, valeric acid, cyclopropanecarboxylic acid, cyclopentanecarboxylic acid, benzoic acid, p-chlorobenzoic acid, phenylacetic acid, nicotinic acid etc.

The term "halo-alkyl" means an alkyl group carrying a halogen substituent, examples of halo-alkyl groups being chloromethyl, 2-chloroethyl, 3-bromopropyl etc. Examples of carboxy-alkyl groups are carboxymethyl, 2-carboxyethyl etc.

The term "alkoxy", alone or in combination as in alkoxycarbonyl, means an alkyl group as defined above which is linked via an oxygen atom. Thus, examples of alkoxy groups are methoxy, ethoxy, propoxy, isopropoxy, butoxy, tert.butoxy, pentyloxy, hexyloxy etc. Examples of alkoxycarbonylamino-alkyl groups are methoxycarbonylaminomethyl, 2-ethoxycarbonylaminoethyl, 3-ethoxycarbonylaminopropyl etc. The alkoxycarbonyl-alkyl group can be, for example, methoxycarbonylmethyl, 2-methoxycarbonylethyl, 3-ethoxycarbonylpropyl etc. The term "aralkoxy" means an aralkyl group as defined above which is linked to the molecule via an oxygen atom, examples of aralkoxy groups being benzyloxy, 4-chlorobenzyloxy, 2-phenylethoxy, 3-phenylpropoxy etc.

Pharmaceutically acceptable salts include any conventional salt suitable for pharmaceutical dosing. The compounds of formula I which are acidic form pharmaceutically acceptable salts upon treatment with bases. Examples of such salts are alkali metal salts (e.g. sodium and potassium salts), alkaline earth metal salts (e.g. calcium and magnesium salts), ammonium salts and salts with organic amines (e.g. dicyclohexylamine salts). The compounds of formula I which are basic form pharmaceutically acceptable salts upon treatment with acids. Examples of such salts are mineral acid salts such as hydrohalides (e.g. hydrobromides, hydrochlorides etc), sulphates, phosphates, nitrates etc and organic acid salts such as the acetates, maleates, fumarates, tartrates, citrates, salicylates, methanesulphonates, p-toluenesulphonates and the like.

$R^1$ in formula I preferably is hydroxy, alkyl, aralkyl or alkoxy. $R^2$ preferably is hydrogen. Preferably, $R^3$ is hydrogen. X preferably is an oxygen, —NH— or —$(CH_2)_n$— in which n is zero or 1.

From the foregoing it will be evident that particularly preferred compounds of formula I hereinbefore are those in which $R^1$ is hydroxy, alkyl, aralkyl or alkoxy, $R^2$ is hydrogen, $R^3$ is hydrogen and X is oxygen, —NH— or —$(CH_2)_n$— in which n is zero or 1.

Especially preferred compounds of formula I are:
Octahydro-9(S)-phosphonomethyl-10-oxo-6H-pyridazo[1,2-a][1,2]diazepine-1(S)-carboxylic acid, octahydro-9(S)-[[(hydroxy)methylphosphinyl]methyl]-6,10-dioxo-6H-pyridazo[1,2-a][1,2]diazepine-1(S)-carboxylic acid, octahydro-9(S)-phosphono-6,10-dioxo-6H-pyridazo[1,2-a][1,2]diazepine-1(S)-carboxylic acid, 9(S)-diethoxyphosphinyl-octahydro-6,10-dioxo-6H-pyridazo[1,2-a][1,2]diazepine-1(S)-carboxylic acid, octahydro-9(S)-[[hydroxy(methoxy)phosphinyl]methyl]-6,10-dioxo-6H-pyridazo[1,2-a][1,2]diazepine-1(S)-carboxylic acid, octahydro-9(S)-phosphonomethyl-6,10-dioxo-6H-pyridazo[1,2-a][1,2]diazepine-1(S)-carboxylic acid, 9(S)-[[hydroxy(3-phenylpropyl)phosphinyl)]methyl]-octahydro-6,10-dioxo-6H-pyridazo[1,2-a][1,2]diazepine-1(S)-carboxylic acid, 9(S)-[[hydroxy(phenethyl)phosphinyl]amino]-octahydro-10-oxo-6H-pyridazo[1,2-a][1,2]diazepine-1(S)-carboxylic acid, 9(S)-[[hydroxy(2-phenethyl)phosphinyl]methyl]-octahydro-10-oxo-6H-pyridazo[1,2-a][1,2]diazepine-1(S)-carboxylic acid and 9(S)-[hydroxy(4-phenylbutyl)phosphinyl]-octahydro-10-oxo-6H-pyridazo[1,2-a][1,2]diazepine-1(S)-carboxylic acid.

Examples of other interesting compounds of formula I are:
Methyl 9(S)-dimethoxyphosphinylmethyl-octahydro-6,10-dioxo-6H-pyridazo[1,2-a][1,2]diazepine-1(S)-carboxylate, methyl 9(S)-dimethoxyphosphinylmethyl-octahydro-10-oxo-6H-pyridazo[1,2-a][1,2]diazepine-1(S)-carboxylate, methyl octahydro-9(S)-phosphonomethyl-10-oxo-6H-pyridazo[1,2-a][1,2]diazepine-1(S)-carboxylate, methyl 9(S)-[[(ethoxy)methylphosphinyl]methyl]-octahydro-6,10-dioxo-6H-pyridazo[1,2-a][1,2]diazepine-1(S)-carboxylate, methyl 9(S)-diethoxyphosphinyl-octahydro-6,10-dioxo-6H-pyridazo[1,2-a][1,2]diazepine-1(S)-carboxylate, methyl 9(S)-diethoxyphosphinylmethyl-octahydro-6,10-dioxo-6H-pyridazo[1,2a][1,2]diazepine-1(S)-carboxylate, methyl 9(S)-[[ethoxy(3-phenylpropyl)phosphinyl]methyl]-octahydro-6,10-dioxo-6H-pyridazo[1,2-a][1,2]diazepine-1(S)-carboxylate, benzyl 9(S)-[[benzyloxy(phenethyl)phosphinylamino]-octahydro-10-oxo-6H-pyridazo[1,2-a][1,2]diazepine-1(S)-carboxylate, tert.butyl 9(S)-(dibenzylphosphonoxy)-octahydro-6,10-dioxo-6H-pyridazo[1,2-a][1,2]diazepine-1(S)-carboxylate, tert.-butyl 9(S)-[benzyloxy(phenethyl)phosphinyloxy]-octahydro-6,10-dioxo-6H-pyridazo[1,2-a][1,2]diazepine-1(S)-carboxylate, benzyl 9(S)-[(dibenzyloxyphosphinyl)amino]-octahydro-10-oxo-6H-pyridazo[1,2-a][1,2[diazepine-1(S)-carboxylate and 9(S)-[dibenzyloxyphosphinyl)amino]-octahydro-10-oxo-6H-pyridazo[1,2-a][1,2]diazepine-1(S)-carboxylic acid.

Further examples of other interesting compounds of formula I are:

Tert.butyl 9(S)-[benzyloxy(4-phenylbutyl)phosphinyloxy]-octahydro-6,10-dioxo-6H-pyridazo[1,2-a][1,2]diazepine-1(S)-carboxylate, 9(S)-[hydroxy(4-phenylbutyl)phosphinyloxy]-octahydro-6,10-dioxo-6H-pyridazo[1,2-a][1,2]diazepine-1(S)-carboxylic acid, benzyl 9(S)-[[benzyloxy(benzyl)phosphinyl]amino]octahydro-10-oxo-6H-pyridazo[1,2-a][1,2]diazepine-1(S)-carboxylate, benzyl 9(S)-[[benzyloxy(3-phenylpropyl)phosphinyl]amino]-octahydro-10-oxo-6H-pyridazo[1,2-a][1,2]diazepine-1(S)-carboxylate, benzyl 9(S)-[[benzyloxy(4-phenylbutyl)phosphinyl]amino]-octahydro-10-oxo-6H-pyridazo[1,2-a][1,2]diazepine-1(S)-carboxylate, 9(S)-[[hydroxy(benzyl)phosphinyl]amino]-octahydro-10-oxo-6H-pyridazo[1,2-a][1,2]diazepine-1(S)-carboxylic acid, 9(S)-[[hydroxy(3-phenylpropyl)phosphinyl]amino]-octahydro-10-oxo-6H-pyridazo[1,2-a][1,2]diazepine-1(S)-carboxylic acid, 9(S)-[[hydroxy(4-phenylbutyl)phosphinyl]amino]-octahydro-10-oxo-6H-pyridazo[1,2-a][1,2]diazepine-1(S)-carboxylic acid, methyl 9(S)-[(ethoxy)(5-phenylpentyl)phosphinyl]-octahydro-6,10-dioxo-6H-pyridazo[1,2-a][1,2]diazepine-1(S)-carboxylate, methyl 9(S)-[(ethoxy)(4-phenylbutyl)phosphinyl]-octahydro-6,10-dioxo-6H-pyridazo[1,2-a][1,2]diazepine-1(S)-carboxylate, methyl 9(S)-[(ethoxy)(3-phenylpropyl)phosphinyl]-octahydro-6,10-dioxo-6H-pyridazo[1,2-a][1,2]diazepine-1(S)-carboxylate, methyl 9(S)-[(ethoxy)(phenethyl)phosphinyl]-octahydro-6,10-dioxo-6H-pyridazo[1,2-a][1,2]diazepine-1(S)-carboxylate, 9(S)-[hydroxy(5-phenylpentyl)phosphinyl]-octahydro-6,10-dioxo-6H-pyridazo[1,2-a][1,2]diazepine-1(S)-carboxylic acid, 9(S)-[hydroxy(4-phenylbutyl)phosphinyl]-octahydro-6,10-dioxo-6H-pyridazo[1,2-a][1,2]diazepine-1(S)-carboxylic acid, 9(S)-[hydroxy(3-phenylpropyl)phosphinyl]-octahydro-6,10-dioxo-6H-pyridazo[1,2-a][1,2diazepine-1(S)-carboxylic acid, 9(S)-[hydroxy(phenethyl)phosphinyl]octahydro-6,10-dioxo-6H-pyridazo[1,2-a][1,2]diazepine-1(S)-carboxylic acid, methyl 9(S)-[[ethoxy(phenethyl)phosphinyl]methyl]octahydro-6,10-dioxo-6H-pyridazo[1,2-a][1,2]diazepine-1(S)-carboxylate, 9(S)-[[hydroxy(phenethyl)phosphinyl]methyl]octahydro-6,10-dioxo-6H-pyridazo[1,2-a][1,2]diazepine-1(S)-carboxylic acid, methyl 9(S)-[[ethoxy(phenethyl)phosphinyl]methyl]octahydro-10-oxo-6H-pyridazo[1,2-a][1,2]diazepine-1(S)-carboxylate, methyl 9(S)-[(ethoxy)(4-phenylbutyl)phosphinyl]-octahydro-10-oxo-6H-pyridazo[1,2-a][1,2]diazepine-1(S)-carboxylate, ethyl 9(S)-[[(4-benzyloxybutyl)(ethoxy)phosphinyl]methyl]-octahydro-6,10-dioxo-6H-pyridazo[1,2-a][1,2]diazepine-1(S)-carboxylate, 9(S)-[[(4-benzyloxybutyl)(hydroxy)phosphinyl]methyl]-octahydro-6,10-dioxo-6H-pyridazo[1,2-a][1,2]diazepine-1(S)-carboxylic acid, 9(S)-[[4-hydroxybutyl)(hydroxy)phosphinyl]methyl]-octahydro-6,10-dioxo-6H-pyridazo[1,2-a][1,2]diazepine-1(S)-carboxylic acid, 9(S)-[[(4-aminobutyl)(ethoxy)phosphinyl]methyl]-octahydro-6,10-dioxo-6H-pyridazo[1,2-a][1,2]diazepine-1(S)-carboxylate, 9(S)-[[(4-aminobutyl)(hydroxy)phosphinyl]methyl]-octahydro-6,10-dioxo-6H-pyridazo[1,2-a][1,2]diazepine-1(S)-carboxylic acid, tert.butyl octahydro-9(S)-[[methoxy(4-nitrophenethyl)phosphinyl]methyl]-6,10-dioxo-6H-pyridazo[1,2-a][1,2]diazepine-1(S)-carboxylate, octahydro-9(S)-[[methoxy(4-nitrophenethyl)phosphinyl]methyl]-6,10-dioxo-6H-pyridazo[1,2-a][1,2]diazepine-1(S)-carboxylic acid, octahydro-9(S)-[[hydroxy(4-nitrophenethyl)phosphinyl]methyl]-6,10-dioxo-6H-pyridazo[1,2-a][1,2]diazepine-1(S)-carboxylic acid, 9(S)-[[(4-aminophenethyl)hydroxyphosphinyl]methyl]-octahydro-6,10-dioxo-6H-pyridazo[1,2-a][1,2]diazepine-1(S)-carboxylic acid, 9(S)-[[(4-aminophenethyl)methoxyphosphinyl]methyl]-octahydro-6,10-dioxo-6H-pyridazo[1,2-a][1,2]diazepine-1(S)-carboxylate acid and octahydro 9(S)-[[(hydroxy)[4-(1-iminoethylamino)-phenethyl]phosphinyl]methyl]-6,10-dioxo-6H-pyridazo[1,2-a][1,2]diazepine-1(S)-carboxylic acid.

According to the process provided by the present invention, the compounds of formula I and their pharmaceutically acceptable salts are manufactured by (a) for the manufacture of a compound of formula I in which $R^1$ represents alkyl, aralkyl, aralkoxy-alkyl, acylamino-alkyl, dialkylamino-alkyl alkoxycarbonylamino-alkyl, alkoxycarbonyl-alkyl, alkoxy or aralkoxy, $R^2$ and $R^3$ each represent alkyl or aralkyl, $R^4$ and $R^5$ together represent oxo and X represents $-(CH_2)_n-$ in which n has the significance given above, reacting a compound of the formula

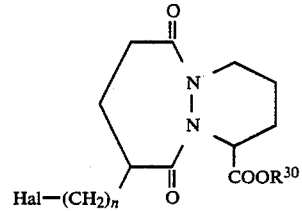

II wherein n has the significance given above, $R^{30}$ represents alkyl or aralkyl and Hal represents a halogen atom, with a compound of the formula

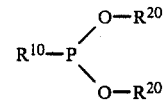

III wherein $R^{10}$ represents alkyl, aralkyl, aralkoxy-alkyl, acylamino-alkyl, dialkylamino-alkyl, alkoxycarbonylamino-alkyl, alkoxycarbonyl-alkyl, alkoxy or aralkoxy and $R^{20}$ represents alkyl or aralkyl, or (b) for the manufacture of a compound of formula I in which $R^1$ represents alkyl, aralkyl, aralkoxy-alkyl, acylamino-alkyl, dialkylamino-alkyl, alkoxycarbonylamino-alkyl, alkoxycarbonyl-alkyl, alkoxy or aralkoxy, $R^2$ and $R^3$ each represent alkyl or aralkyl and X represents an oxygen atom or the group —NR$^6$— in which R$^6$ represents hydrogen, alkyl or aralkyl, reacting a compound of the formula

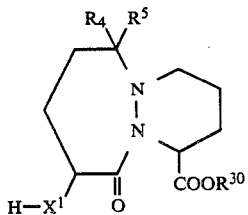

IV wherein R$^4$, R$^5$ and R$^{30}$ have the significance given above and X$^1$ represents an oxygen atom or the group —NR$^6$—, in which R$^6$ has the significance given above, with a compound of the formula

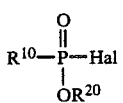

V wherein R$^{10}$, R$^{20}$ and Hal have the significance given above, or (c) for the manufacture of a compound of formula I in which R$^2$ represents alkyl or aralkyl, R$^4$ and R$^5$ together represent oxo and X represents —CH$_2$—, reacting a compound of the formula

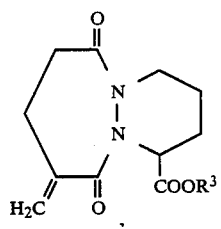

VI wherein R$^3$ has the significance given above, with a compound of the formula

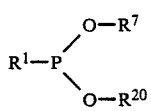

VII wherein R$^1$ and R$^{20}$ have the significance given above and R$^7$ represents alkyl, aralkyl or trialkylsilyl.

or (d) for the manufacture of a compound of formula I in which R$^1$ represents alkyl, aralkyl, aralkoxy-alkyl, amino-alkyl, acylamino-alkyl, monoalkylamino-alkyl, dialkylamino-alkyl, alkoxycarbonylamino-alkyl, alkoxycarbonyl-alkyl, alkoxy or aralkoxy, R$^2$ and R$^3$ each represent alkyl or aralkyl, and R$^4$ and R$^5$ each represent a hydrogen atom, reducing a compound of formula I in which R$^1$ represents alkyl, aralkyl, aralkoxy-alkyl, amino-alkyl, acylamino-alkyl, monoalkylamino-alkyl, dialkylamino-alkyl, alkoxycarbonylamino-alkyl, alkoxycarbonyl-alkyl, alkoxy or aralkoxy, R$^2$ and R$^3$ each represent alkyl or aralkyl, and R$^4$ and R$^5$ together represent oxo, or (e) for the manufacture of a compound of formula I in which R$^1$ represents hydroxy, alkoxy or aralkoxy, R$^2$ represents hydrogen, alkyl or aralkyl and/or R$^3$ represents hydrogen, alkyl or aralkyl, with the proviso that either R$^1$ represents hydroxy and/or at least one of R$^2$ and R$^3$ represents hydrogen, appropriately de-esterifying a compound of formula I in which R$^1$ represents hydroxy, alkoxy or aralkoxy, R$^2$ represents hydrogen, alkyl or aralkyl and/or R$^3$ represents hydrogen, alkyl or aralkyl, with the proviso that either R$^1$ represents other than hydroxy and/or at least one of R$^2$ and R$^3$ represents other than hydrogen, or (f) for the manufacture of a compound of formula I in which R$^1$ represents alkyl, aralkyl, aralkoxy-alkyl, hydroxy-alkyl, amino-alkyl, acylamino-alkyl, monoalkylamino-alkyl, dialkylamino-alkyl, alkoxycarbonylamino-alkyl, halo-alkyl, carboxy-alkyl, alkoxycarbonyl-alkyl, alkoxy or aralkoxy, R$^2$ and R$^3$ each represent alkyl or aralkyl and X represents the group —NR$^{61}$— in which R$^{61}$ represents alkyl or aralkyl, alkylating or aralkylating a compound of formula I in which R$^1$ represents alkyl, aralkyl, aralkoxy-alkyl, hydroxy-alkyl, amino-alkyl, acylamino-alkyl, monoalkylamino-alkyl, dialkylamino-alkyl, alkoxycarbonylamino-alkyl, halo-alkyl, carboxy-alkyl, alkoxycarbonyl-alkyl, alkoxy or aralkoxy, R$^2$ and R$^3$ each represent alkyl or aralkyl and X represents the group —NH—, or (g) for the manufacture of a compound of formula I in which R$^1$ represents alkyl, aralkyl, aralkoxy-alkyl, hydroxy-alkyl, amino-alkyl, acylamino-alkyl, monoalkylamino-alkyl, dialkylamino-alkyl, alkoxycarbonylamino-alkyl, halo-alkyl, carboxy-alkyl, alkoxycarbonyl-alkyl, alkyl or aralkyl, R$^2$ represents alkyl or aralkyl and R$^3$ represents alkyl or aralkyl, appropriately esterifying a compound of formula I in which R$^1$ represents alkyl, aralkyl, aralkoxy-alkyl, hydroxy-alkyl, amino-alkyl, acylamino-alkyl, monoalkylamino-alkyl, dialkylamino-alkyl, alkoxycarbonylamino-alkyl, halo-alkyl, carboxy-alkyl, alkoxycarbonyl-alkyl, alkyl or aralkyl, R$^2$ represents alkyl or aralkyl and R$^3$ represents hydrogen, or (h) for the manufacture of a compound of formula I in which R$^1$ represents hydroxy-alkyl and R$^2$ and R$^3$ each represent hydrogen or alkyl, catalytically hydrogenating a compound of formula I in which R$^1$ represents aryloxy-alkyl and R$^2$ and R$^3$ each represent hydrogen or alkyl, or (i) for the manufacture of a compound of formula I in which R$^1$ represents halo-alky and R$^2$ and R$^3$ each represent alkyl or aralkyl, halogenating a compound of formula I in which R$^1$ represents hydroxy-alkyl and R$^2$ and R$^3$ each represent alkyl or aralkyl, or (j) for the manufacture of a compound of formula I in which R$^1$ represents amino-alkyl or monoalkylamino-alkyl and R$^2$ and R$^3$ each represent alkyl or aralkyl, converting the hydroxy-alkyl group in a compound of formula I in which R$^1$ represents hydroxy-alkyl and R$^2$ and R$^3$ each represent alkyl or aralkyl into an amino-alkyl or monoalkylamino-alkyl group, or (k) for the manufacture of a compound of formula I in which R$^1$ represents amino-alkyl or monoalkylamino-alkyl and R$^2$ and R$^3$ each represent alkyl or aralkyl, reacting a compound of formula I in which R$^1$ represents halo-alkyl and R$^2$ and R$^3$ each represent alkyl or aralkyl with ammonia or a monoalkylamine, or (l) for the manufacture of a compound of formula I in which R$^1$ represents acylamino-alkyl and R$^2$ and R$^3$ each represent alkyl or aralkyl, acylating a compound of formula I in which $R^1$ represents amino-alkyl and $R^2$ and $R^3$ each represent alkyl or aralkyl, or (m) for the manufacture of a compound of formula I in which $R^1$ represents carboxy-alkyl and $R^2$ and $R^3$ each represent alkyl or aralkyl, oxidizing a compound of formula I in which $R^1$ represents hydroxy-alkyl and $R^2$ and $R^3$ each represent alkyl or aralkyl, and (n) if desired, reducing a nitro-substituted phenyl group present in $R^1$ in a compound of formula I to an amino-substituted phenyl group, and/or (o) if desired, converting an amino-substituted phenyl group present in $R^1$ in a compound of formula I into an iminoalkylamino group by reaction with an alkyl cyanide in the presence of a trialkylsilyl halide, and/or (p) if desired, separating a mixture of diastereoisomeric racemates obtained into the diastereoisomeric racemates of optically pure diastereoisomers, and/or (q) if desired, resolving a racemate obtained into the optical antipodes, and (r) if desired, converting a compound of formula I obtained into a pharmaceutically acceptable salt.

The reaction of a compound of formula II with a compound of formula III in accordance with embodiment (a) of the process can be carried out in the presence or absence of an inert organic solvent. When an inert organic solvent is used this can suitably be, for example, a hydrocarbon such as benzene, toluene etc, a halogenated hydrocarbon such as dichloromethane, chlorobenzene etc, an amide such as dimethylformamide or the like. Conveniently, the reaction is carried out at an elevated temperature, preferably at the reflux temperature of the reaction mixture. In certain circumstances it can be advantageous to carry out the reaction under an inert gas atmosphere (e.g. nitrogen, argon etc). Hal in the compound of formula II preferably represents a bromine atom.

The reaction of a compound of formula IV with a compound of formula V in accordance with embodiment (b) of the process can be carried out in a known manner in the presence of a base and an inert organic solvent at about room temperature. For example, when a compound of formula IV in which $X^1$ represents an oxygen atom is used, the reaction can suitably be carried out by firstly treating this compound with an alkali metal hydride such as sodium hydride in an inert organic solvent such as a cyclic ether (e.g. tetrahydrofuran) and then adding the compound of formula V, conveniently dissolved in the same organic solvent. Again, for example, when a compound of formula IV in which $X^1$ represents the group —$NR^6$— is used, the reaction can suitably be carried out in the presence of a tertiary amine such as a tri(lower alkyl)amine (e.g. triethylamine, diisopropylethylamine, etc) and in an inert organic solvent such as a halogenated hydrocarbon (e.g. dichloromethane, chloroform, carbon tetrachloride etc).

The reaction of a compound of formula VI with a compound of formula VII in accordance with embodiment (c) of the process can be carried out in the presence or absence of an inert organic solvent. When a solvent is used, this can conveniently be a halogenated hydrocarbon (e.g. dichloromethane, chloroform, chlorobenzene etc) or an aromatic hydrocarbon (e.g. benzene, toluene, a xylene etc). The reaction is conveniently carried out at a temperature between about 20° C. and about 150° C. Suitably, the reaction is carried out under an inert gas atmosphere such as nitrogen, argon etc. When a compound of formula VII in which $R^7$ represents trialkylsilyl (e.g. trimethylsilyl) is used, this compound can conveniently be formed in situ. In certain circumstances, depending on the reaction conditions employed, when a compound of formula VI in which $R^3$ represents hydrogen is reacted with a compound of formula VII in which $R^7$ represents alkyl or aralkyl, there is obtained a compound of formula I in which $R^3$ represents alkyl or aralkyl.

The reduction of a compound of formula I in which $R^1$ represents alkyl, aralkyl, aralkoxy-alkyl, amino-alkyl, acylamino-alkyl, monoalkylamino-alkyl, dialkylamino-alkyl, alkoxycarbonylamino-alkyl, alkoxycarbonyl-alkyl, alkoxy or aralkoxy, $R^2$ represents alkyl or aralkyl, $R^3$ represents alkyl or aralkyl and $R^4$ and $R^5$ together represent oxo in accordance with embodiment (d) of the process is suitably carried out using a complex of borane such as a borane/tetrahydrofuran, borane/dimethyl sulphide, borane/N,N-diethylaniline or like complex. This reduction is conveniently carried out in an inert organic solvent and at room temperature or a temperature below room temperature; for example, using a borane/tetrahydrofuran complex in tetrahydrofuran at about 0° to about 20° C.

The de-esterification of a compound of formula I in which $R^1$ represents alkoxy or aralkoxy, $R^2$ represents alkyl or aralkyl and/or $R^3$ represents alkyl or aralkyl in accordance with embodiment (e) of the process can be carried out according to methods known per se. For example, a compound of formula I in which $R^1$ represents alkoxy or aralkoxy and $R^2$ represents alkyl or aralkyl can be converted into a corresponding compound of formula I in which $R^1$ represents hydroxy and $R^2$ represents hydrogen by treatment with trimethylsilyl bromide, conveniently at about room temperature. Again, for example, a compound of formula I in which $R^1$ represents alkoxy or aralkoxy and $R^2$ represents alkyl or aralkyl can be converted into a corresponding compound of formula I in which $R^1$ represents alkoxy or aralkoxy and $R^2$ represents hydrogen by treatment with lithium thiocyanate, conveniently in an inert organic solvent such as an aliphatic ketone (e.g. acetone, 2-butanone etc) and at an elevated temperature, for example at the reflux temperature of the reaction mixture. The conversion of a compound of formula I in which $R^3$ represents alkyl or aralkyl into a corresponding compound of formula I in which $R^3$ represents hydrogen can be carried out, for example, by treatment with a base or, where the alkyl group is tert.butyl, by treatment with acid. Suitable bases which can be used are alkali metal hydroxides (e.g. sodium hydroxide, potassium hydroxide etc) and ammonium hydroxide, and the treatment can be carried out at a temperature between about room temperature and the boiling point of the reaction mixture, advantageously at about room temperature. Anhydrous trifluoroacetic acid is an especially suitable acid for the de-esterification of a compound of formula I in which $R^3$ represents tert.butyl, with the treatment in this case being expediently carried out at about room temperature. A compound of formula I in which $R^3$ represents aralkyl can also be converted into a corresponding compound of formula I in which $R^3$ represents hydrogen by hydrogenolysis in a manner known per se.

The alkylation or aralkylation of a compound of formula I in which $R^1$ represents alkyl, aralkyl, aralkoxy-alkyl, hydroxy-alkyl, amino-alkyl, acylamino-alkyl, monoalkylamino-alkyl, dialkylamino-alkyl, alkoxycarbonylamino-alkyl, halo-alkyl, carboxy-alkyl, alkoxycarbonyl-alkyl, alkoxy or aralkoxy, $R^2$ represents alkyl or aralkyl, $R^3$ represents alkyl or aralkyl and X represents the group —NH— in accordance with embodiment (f) of the process can be carried out in a manner known per se. For example, the compound of formula I can be reacted with an appropriate alkyl halide (e.g. methyl bromide, ethyl chloride etc) or an appropriate aralkyl halide (e.g. benzyl bromide etc) in the presence of a base.

The esterification in accordance with embodiment (g) of the process can be carried out according to methods known per se. For example, the esterification can be carried out by reaction with an appropriate alcohol (e.g. methanol, ethanol, benzyl alcohol etc) in the presence of a mineral acid (e.g. hydrochloric acid etc) or with a suitable diazoalkane (e.g. diazomethane, phenyldiazomethane etc). A further method for the formation of a tert.butyl ester comprises carrying out the esterification using isobutene in the presence of sulphuric acid.

The catalytic hydrogenation in accordance with embodiment (h) of the process can be carried out in a known manner; for example, in the presence of a noble metal catalyst such as a palladium catalyst in an inert organic solvent (e.g. an alkanol such as ethanol etc), conveniently at about room temperature and atmospheric pressure.

Conventional methods can be used for the halogenation in accordance with embodiment (i) of the process. For example, the halogenation can be carried out by treatment with a suitable halogenating agent such as a thionyl halide (e.g. thionyl chloride etc), a phosphorus halide (e.g. phosphorus trichloride, phosphorus pentachloride etc) or the like. Alternatively, the halogenation can be carried out by firstly converting the compound of formula I in which $R^1$ represents hydroxy-alkyl and $R^2$ and $R^3$ each represent alkyl or aryl into the corresponding alkylsulphonate (e.g. mesylate) or arylsulphonate (e.g. tosylate) and then reacting this with an alkali metal halide (e.g. sodium fluoride, sodium chloride, lithium chloride etc) in acetone or with a pyridine hydrohalide at a temperature between about 0° C. and 100° C.

The conversion of the hydroxy group in a compound of formula I in which $R^1$ represents hydroxy-alkyl and $R^2$ and $R^3$ each represent alkyl or aralkyl into an aminoalkyl or monoalkylamino-alkyl group in accordance with embodiment (j) of the process can be carried out according to methods know per se. For example, such a compound can be firstly converted into the corresponding alkylsulphonate (e.g. mesylate) or arylsulphonate (e.g. tosylate) which is then reacted with ammonia or an appropriate monoalkylamine (e.g. methylamine, ethylamine etc). Alternatively, the alkylsulphonate or arylsulphonate can be reacted with an alkali metal azide (e.g. sodium azide) in a known manner, for example in an inert organic solvent such as 2-butanone and at an elevated temperature (e.g. the reflux temperature of the reaction mixture) to give the corresponding azido-alkyl compound which can then be converted into the desired amino-alkyl compound by catalytic hydrogenation in a manner known per se.

The reaction of a compound of formula I in which $R^1$ represents halo-alkyl and $R^2$ and $R^3$ each represent alkyl or aralkyl with ammonia or a monoalkylamine (e.g. methylamine, ethylamine etc) in accordance with embodiment (k) of the process can be carried out according to conventional methods; for example in an inert organic solvent and in the presence of a suitable acid-binding agent.

Conventional methods can be used for the acylation of a compound of formula I in which $R^1$ represents amino-alkyl and $R^2$ and $R^3$ each represent alkyl or aralkyl in accordance with embodiment (l) of the process. For example, the acylation can be carried out using an appropriate acyl halide (e.g. an acyl chloride such as acetyl chloride) in the presence of an appropriate acid-binding agent.

The oxidation in accordance with embodiment (m) of the process can be carried out according to methods known per se; for example, by treatment with an appropriate oxidizing agent such as an alkali metal dichromate (e.g. potassium dichromate etc).

The reduction of a nitro-substituted phenyl group to an amino-substituted phenyl group in accordance with embodiment (n) of the process can be carried out in a manner known per se; for example by catalytic hydrogenation in the presence of a noble-metal catalyst such as a palladium catalyst (e.g. palladium-on-carbon) in an inert organic solvent (e.g. an alkanol such as methanol, ethanol etc).

The conversion of an amino-substituted phenyl group into an iminoalkylamino group in accordance with embodiment (o) of the process is conveniently carried out using excess alkyl cyanide (e.g. acetonitrile, propionitrile etc), whereby this also serves as the solvent. The preferred trialkylsilyl halide is trimethylsilyl bromide, although other trialkylsilyl halides such as trimethylsilyl chloride etc can also be used. The reaction is suitably carried out at about room temperature.

The separation of diastereoisomer mixtures into the diastereoisomeric racemates or optically pure diastereoisomers in accordance with embodiment (p) of the process can be carried out according to methods known per se; for example, by chromatography (e.g. on silica gel) using a suitable solvent system (e.g. ethyl acetate/n-hexane).

The resolution of a racemate into the optical antipodes in accordance with embodiment (q) of the process can also be carried out according to methods known per se; for example, by treatment with an appropriate optically active acid or an appropriate optically active base as the case may require, separating the optically active salts obtained (e.g. by fractional crystallization) and, where required, liberating the optically uniform compounds from these salts by conventional methods.

The conversion of a compound of formula I into a pharmaceutically acceptable salt in accordance with embodiment (r) of the process can be carried out in a manner known per se. For example, a compound of formula I which is acidic can be converted into a pharmaceutically acceptable salt by treatment with an appropriate base such as an alkali metal hydroxide (e.g. sodium hydroxide, potassium hydroxide etc), an alkaline earth metal hydroxide (e.g. calcium hydroxide, magnesium hydroxide etc), ammonium hydroxide or an organic amine (e.g. dicyclohexylamine etc) again for example, a compound of formula I which is basic can be converted into a pharmaceutically acceptable salt by treatment with an acid such as a mineral acid (e.g. a hydrohalic acid such as hydrobromic acid, hydrochloric acid etc, sulphuric acid, phosphoric acid, nitric acid etc) or an organic acid such as acetic acid, maleic acid, fumaric acid, tartaric acid, citric acid, salicylic acid, methanesulphonic acid, p-toluenesulphonic acid etc.

The compounds of formula II in which n stands for zero, which are used as starting materials in embodiment (a) of the process, are known compounds.

The compounds of formula II in which n stands for 1 or 2, which are also used as starting materials in embodiment (a) of the process, are novel compounds which have the formula

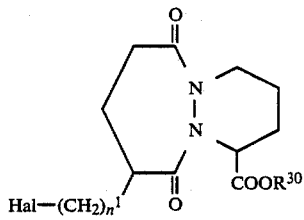

wherein $R^{30}$ is alkyl or aralkyl, Hal is halogen and $n^1$ is 1 or 2.

The compounds of formula IIa can be prepared, for example, by reacting a compound of the formula

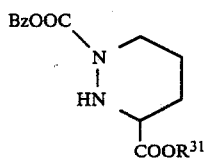

wherein $R^{31}$ represents alkyl and Bz represents benzyl, with a compound of the formula

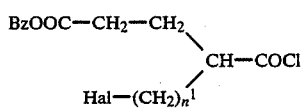

wherein Bz and Hal have the significance given above and $n^1$ stands for 1 or 2, removing the benzyl and benzyloxycarbonyl groups from the resulting compound of the formula

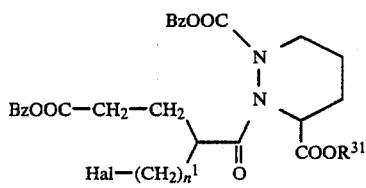

wherein $R^{31}$, Bz, Hal and $n^1$ have the significance given above. and cyclizing the resulting acid of the formula

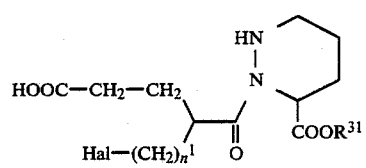

wherein $R^{31}$, Hal and $n^1$ have the significance given above, and, where a compound of formula II in which n stands for 1 or 2 and $R^{30}$ represents aralkyl is required, de-esterifying the resulting compound of formula II in which n stands for 1 or 2 and $R^{30}$ represents alkyl and esterifying the resulting acid to give the corresponding aralkyl ester.

The reaction of a compound of formula VIII with a compound of formula IX can be carried out in a conventional manner; for example, in an inert organic solvent (e.g. a halogenated hydrocarbon such as dichloromethane) and in the presence of a base (e.g. an alkali metal carbonate such as sodium carbonate or an alkali metal bicarbonate such as sodium bicarbonate), suitably at about room temperature.

The removal of the benzyl and benzyloxycarbonyl groups from a compound of formula X can be carried out according to generally known methods; for example, using hydrogen in the presence of a noble-metal catalyst (e.g. palladium-on-carbon) or, when $R^{30}$ represents other than tert.butyl, using hydrogen bromide in glacial acetic acid.

The cyclization of an acid of formula XI can be carried out in a manner known per se. In a preferred procedure, the cyclization is carried out by converting an acid of formula XI by treatment in a known manner with an appropriate halogenating agent such as a phosphorus pentahalide (e.g. phosphorus pentachloride etc) or a thionyl halide (e.g. thionyl chloride etc) into the corresponding acid halide (e.g. acid chloride) which cyclizes spontaneously to the compound of formula II in which n stands for 1 or 2 and $R^{30}$ represents alkyl.

The de-esterification of a compound of formula II in which n stands for 1 or 2 and $R^{30}$ represents alkyl to give the corresponding acid, i.e. a compound corresponding to formula II, but in which $R^{30}$ represents hydrogen, can be carried out, for example, by treatment with a base or, where the alkyl group is tert.butyl, by treatment with acid. Suitable bases which can be used are alkali metal hydroxides (e.g. sodium hydroxide, potassium hydroxide etc) and ammonium hydroxide, and the treatment can be carried out at a temperature between about room temperature and the boiling point of the reaction mixture, advantageously at about room temperature. Anhydrous trifluoroacetic acid is an especially suitable acid for the de-esterification of a compound of formula II in which $R^{30}$ represents tert.butyl, with the treatment in this case being expediently carried out at about room temperature.

The esterification of the thus-obtained acid can be carried out according to methods known per se; for example by reaction with an appropriate alcohol (e.g. benzyl alcohol etc) in the presence of a mineral acid (e.g. hydrochloric acid etc) or with a suitable diazoalkane (e.g. phenyldiazomethane etc).

The compounds of formula II in which n stands for 1 can also be prepared, for example, by cleaving off the benzyloxycarbonyl group from a compound of formula VIII above, reacting the resulting compound of the formula

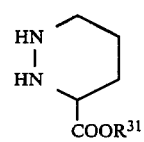

wherein $R^{31}$ has the significance given above, with α-methylene-glutaric anhydride, cyclizing the resulting compound of the formula

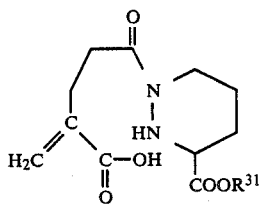

wherein $R^{31}$ has the significance given above, replacing a tert.butyl group $R^{31}$ by a different alkyl group in the resulting compound of the formula

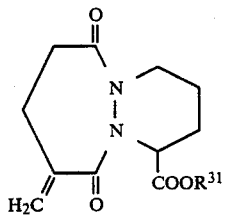

wherein $R^{31}$ has the significance given above, treating the compound of formula VIa in which $R^{31}$ represents alkyl other than tert.butyl with hydrogen halide and, where a compound of formula II in which $R^{30}$ represents tert.butyl or aralkyl is required, de-esterifying the resulting compound of formula II in which n stands for 1 and $R^{30}$ represents alkyl other than tert.butyl and esterifying the resulting acid to give the corresponding tert.butyl or aralkyl ester.

The cleavage of the benzyloxycarbonyl group from a compound of formula VIII can be carried out according to known procedures, for example using hydrogen in the presence of a catalyst such as a noble-metal catalyst (e.g. palladium-on-carbon) and in the presence of an inert organic solvent (e.g. an alkanol such as methanol etc).

The reaction of a thus-obtained compound of formula XII with α-methylene-glutaric anhydride to give a compound of formula XIII is expediently carried out in an inert organic solvent such as a halogenated hydrocarbon (e.g. dichloromethane etc) or an ether (e.g. dioxan, tetrahydrofuran etc) at a temperature between about room temperature and the reflux temperature of the reaction mixture, preferably at about room temperature.

The cyclization of a compound of formula XIII can be carried out in a manner known per se. In a preferred procedure, the cyclization is carried out by converting a compound of formula XIII by treatment in a known manner with an appropriate halogenating agent such as a phosphorus pentahalide (e.g. phosphorus pentachloride etc) or a thionyl halide (e.g. thionyl chloride etc) into the corresponding acid halide (e.g. acid chloride) which cyclizes spontaneously to give a compound of formula VIa.

When $R^{31}$ in the cyclization product of formula VIa represents tert.butyl, this is replaced by a different alkyl group before the treatment with hydrogen halide. This replacement is carried out by treatment with anhydrous trifluoroacetic acid to give the free acid which is then esterified to give an alkyl ester other than the tert.butyl ester.

A thus-obtained compound, i.e. a compound of formula VIa in which $R^{31}$ does not represent tert.butyl, is then treated with hydrogen halide to give a compound of formula II in which n stands for 1 and $R^{30}$ represents other than tert.butyl. Hydrogen bromide is the preferred hydrogen halide. Preferably, the treatment is carried out in an inert organic solvent such as a halogenated hydrocarbon (e.g. dichloromethane etc) at about room temperature (about about 20° C.).

The de-esterification of a compound of formula II in which n stands for 1 and $R^{30}$ represents other than tert.butyl can be carried out in a known manner by treatment with a base. Suitable bases are alkali metal hydroxides (e.g. sodium hydroxide, potassium hydroxide etc) and ammonium hydroxide. Suitably, the treatment is carried out at a temperature between about room temperature and the boiling point of the reaction mixture, advantageously at about room temperature.

The conversion of a resulting acid into a tert.butyl ester can be carried out in a manner known per se; for example, by reaction with isobutene in the presence of sulphuric acid. The esterification of a resulting acid to give an aralkyl ester can be carried out in a manner analogous to that described earlier.

The compounds of formula II in which n stands for 1 or 2 form an object of the present invention.

The compounds of formula III, which are used as starting materials in embodiment (a) of the process, are known compounds.

The compounds of formula IV in which $X^1$ represents an oxygen atom or the group $-NR^{61}-$ in which $R^{61}$ represents alkyl or alkyl, which are used as starting materials in embodiment (b) of the process are novel and also form an object of the present invention. These compounds have the formula

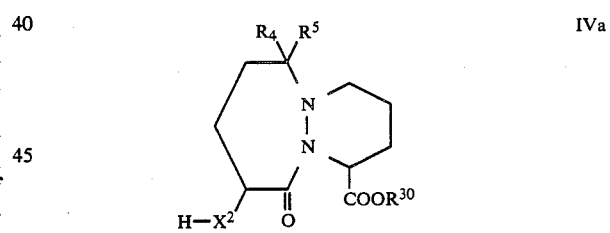

wherein $R^4$ and $R^5$ each are hydrogen or $R^4$ and $R^5$ together are oxo; $R^{30}$ is alkyl or aralkyl; and $X^2$ is oxygen or $-NR^{61}-$ in which $R^{61}$ is alkyl or aralkyl.

The compounds of formula IV in which $X^1$ represents an oxygen atom and $R^{30}$ represents alkyl can be prepared, for example, by reacting a compound of formula VIII with a compound of the formula

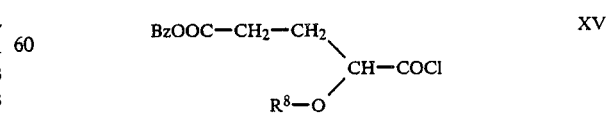

wherein Bz has the significance given above and $R^8$ represents an alkanoyl group (e.g. acetyl), removing the benzyl and benzyloxycarbonyl groups from the resulting compound of the formula

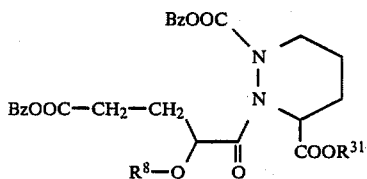

wherein $R^8$, $R^{31}$ and Bz have the significance given above, cyclizing the resulting acid of the formula

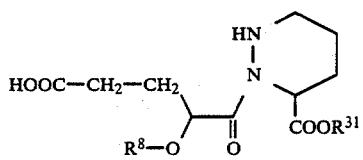

wherein $R^8$ and $R^{31}$ have the significance given above, and cleaving off the alkanoyl group from the thus-obtained compounds of the formula

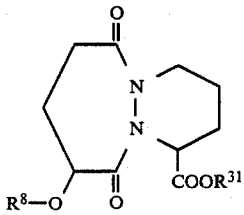

wherein $R^8$ and $R^{31}$ have the significance given above, or, where a compound of formula IV in which $X^1$ represents an oxygen atom and $R^4$ and $R^5$ each represent hydrogen is required, reducing the resulting compound of formula XVIII and subsequently cleaving off the alkanoyl group.

The reaction of a compound of formula VIII with a compound of formula XV can be carried out in a conventional manner; for example, in an inert organic solvent (e.g. a hydrocarbon such as toluene) and in the presence of a base (e.g. an alkali metal carbonate such as sodium carbonate or an alkali metal bicarbonate such as sodium bicarbonate), conveniently at about room temperature.

The removal of the benzyl and benzyloxycarbonyl groups from a compound of formula XVI can be carried out in a manner known per se; for example, using hydrogen in the presence of a noble-metal catalyst (e.g. palladium-on-carbon).

The cyclization of an acid of formula XVII can be carried out in a manner known per se. In a preferred procedure, the cyclization is carried out by converting an acid of formula XVII by treatment in a known manner with an appropriate halogenating agent such as a phosphorus pentahalide (e.g. phosphorus pentachloride etc) or a thionyl halide (e.g. thionyl chloride etc) into the corresponding acid halide (e.g. acid chloride) which cyclizes spontaneously to the compound of formula XVIII.

The cleavage of the alkanoyl group from a compound of formula XVIII can be carried out in a conventional manner; for example, by treatment with an appropriate base such as an alkali metal hydroxide (e.g. sodium hydroxide etc) in an inert organic solvent (e.g. an alkanol such as methanol, ethanol etc), conveniently at about room temperature.

When a compound of formula IV in which $X^1$ represents an oxygen atom and $R^4$ and $R^5$ each represent hydrogen is desired, a compound of formula XVIII is reduced and the alkanoyl group is cleaved off from the product obtained. The reduction is suitably carried out using a complex of borane such as a borane/tetrahydrofuran, borane/dimethyl sulphide, borane/N,N-diethylaniline or like complex. This reduction is conveniently carried out in an inert organic solvent and at room temperature or a temperature below room temperature; for example, using a borane/tetrahydrofuran complex in tetrahydrofuran at about 0° C. to about 20° C. The cleavage of the alkanoyl group is carried out in the manner described previously.

The compounds of formula IV in which $X^1$ represents an oxygen atom and $R^{30}$ represents aralkyl can be prepared, for example, by de-esterifying a compound of formula IV in which $X^1$ represents an oxygen atom and $R^{30}$ represents alkyl and esterifying the resulting acid to give the corresponding aralkyl ester.

The de-esterification of a compound of formula IV in which $X^1$ represents an oxygen atom and $R^{30}$ represents alkyl to give the corresponding acid, i.e. a compound of formula IV, in which $R^{30}$ represents hydrogen, can be carried out, for example, by treatment with a base or, where the alkyl group is tert.butyl, by treatment with acid. Suitable bases which can be used are alkali metal hydroxides (e.g. sodium hydroxide, potassium hydroxide etc) and ammonium hydroxide, and the treatment can be carried out at a temperature between about room temperature and the boiling point of the reaction mixture, advantageously at about room temperature. Anhydrous trifluoroacetic acid is an especially suitable acid for the de-esterification of a compound of formula IV in which $R^{30}$ represents tert.butyl, with the treatment in this case being expediently carried out at about room temperature.

The esterification of the thus-obtained acid can be carried out according to methods known per se; for example by reaction with an appropriate alcohol (e.g. benzyl alcohol etc) in the presence of a mineral acid (e.g. hydrochloric acid etc) or with a suitable diazoalkane (e.g. phenyldiazomethane etc).

The compounds of formula IV in which $X^1$ represents the group —NH—, which are used as starting materials in embodiment (b) of the process, are known compounds.

The compounds of formula IV in which $X^1$ represents the group —$NR^{61}$— in which $R^{61}$ represents alkyl or aralkyl, can be prepared, for example, by appropriately alkylating or aralkylating a corresponding compound of formula IV in which $X^1$ represents the group —NH—. The alkylation of aralkylation can be carried out in a manner known per se. For example, the compound of formula IV in which $X^1$ represents the group —NH— can be reacted with an appropriate alkyl halide (e.g. methyl chloride, ethyl bromide etc) or an appropriate aralkyl halide (e.g. benzyl bromide etc) in the presence of a base.

The compounds of formula V, which are used as starting materials in embodiment (b) of the process, are known compounds or analogues of known compounds which can be prepared in an analogous manner to the known compounds.

The compounds of formula VI, which are used as starting materials in embodiment (c) of the process are known compounds or analogues of known compounds which can be prepared in an analogous manner to the known compounds. Those in which $R^3$ represents alkyl correspond to the compounds of formula VIa given above. The compounds of formula VI in which $R^3$ represents hydrogen can be prepared from the compounds of formula VIa in a manner known per se by treatment with a base or where $R^{31}$ in formula VIa represents tert.butyl, by treatment with anhydrous trifluoroacetic acid. The compounds of formula VI in which $R^3$ represents aralkyl can be prepared from the compounds of formula VI in which $R^3$ represents hydrogen by esterification in a manner known per se; for example, using an appropriate alcohol (e.g. benzyl alcohol etc) in the presence of a mineral acid (e.g. hydrochloric acid etc) or using a suitable diazoalkane (e.g. phenyldiazomethane etc).

The compounds of formula VII, which are also used as starting materials in embodiment (c) of the process, are known compounds or analogues of known compounds which can be prepared in an analogous manner to the known compounds.

The compounds of formula I and their aforementioned pharmaceutically acceptable salts are useful as antihypertensive agents. They inhibit angiotensin converting enzyme (ACE) which brings about the conversion of angiotensin I into angiotensin II and are therefore useful in reducing or alleviating angiotensin-related hypertension.

The activity of the present compounds in inhibiting angiotensin converting enzyme in vitro can be determined by the following test.

The method used is based on the method of Cushman and Cheung (Biochem. Pharmacol., 20. 1637–1648) incorporating the modifications introduced by Hayakari et al (Anal. Biochem., 84. 361-369). The substrate (hippuryl-histidylleucine, 2 mM) is incubated with angiotensin converting enzyme in the presence or absence of various concentrations of test substance in potassium phosphate buffer (pH 8.3; 100 mM) containing sodium chloride (300 mM) for 24 minutes at 37° C. (total value 500 μl). (if the test substance is an ester, it is appropriate to cleave it by means of hog liver esterase before carrying out the test). The reaction is terminated by the addition of 3 ml of potassium phosphate buffer (pH 8.3; 200 mM) at 0° C. 2,4,6-Trichloro-s-triazine (3%) in 1.5 ml of dioxan is added and the mixture is agitated until the yellow chromophore has developed fully. The samples are then centrifuged to remove any precipitate which has formed. The yellow chromophore formed by the reaction of the 2,4,6-trichloro-s-triazine with free hippuric acid is measured spectrophotometrically at 382 nm. $IC_{50}$ values are defined as the concentration of test substance which reduces by 50% the cleavage of hippuryl-histidyl-leucine by angiotensin converting enzyme under the aforementioned conditions.

The results obtained in the foregoing test using representative compounds provided by the invention as the test substance are compiled in the following Table:

TABLE

| Compound | $IC_{50}$ (nM) |
| --- | --- |
| A | 9.6 |
| B | 5.0 |
| C | 2.4 |

TABLE-continued

| Compound | $IC_{50}$ (nM) |
| --- | --- |
| D | 14.0 |

Compound A = Octahydro-9(S)—phosphonomethyl-10-oxo-6H—pyridazo[1,2-a][1,2]diazepine-1(S)—carboxylic acid The compounds of formula I and their aforementioned pharmaceutically acceptable salts can be used as medicaments in the form of pharmaceutical preparations which contain them in association with a compatible pharmaceutical carrier material. This carrier material can be an organic or inorganic carrier material which is suitable for enteral (e.g. oral) or parenteral administration, examples of such carrier materials being water, gelatin, gum arabic, lactose, starch, magnesium stearate, talc, vegetable oils, polyalkylene glycols, petroleum jelly etc. The pharmaceutical preparations can be made up in a solid form (e.g. as tablets, dragees, suppositories or capsules) or in a liquid form (e.g. as solutions, suspensions or emulsions). The pharmaceutical preparations may be subjected to standard pharmaceutical operations such as sterilization and/or may contain adjuvants such as preserving, stabilizing, wetting or emulsifying agents, salts for varying the osmotic pressure or buffers. The pharmaceutical preparations may also contain other therapeutically valuable substances.

The compounds of formula I and their aforementioned pharmaceutically acceptable salts can be administered to adults in a daily dosage of from about 0.1 mg to about 100 mg, preferably about 1 mg to about 50 mg, per kilogram body weight. The daily dosage may be administered as a single dose or in divided doses. It will be appreciated that the aforementioned dosage range is given by way of example only and can be varied upwards or downwards depending on factors such as the particular compound or salt being administered, the route of administration, the severity of the indication being treated and the condition of the patient as determined by the attending physician.

The following Examples illustrate the present invention. Unless otherwise stated, percentages and ratios relating to solvent mixtures are expressed in volume and the remaining percentages and ratios are expressed in weight, temperatures are in degrees Celsius (°C.), normal pressure is about 1 atmosphere and room temperature is about 20° C. Unless otherwise indicated (for example, by a present or future tense verb) the Examples were carried out as written.

EXAMPLE 1

1 g of methyl 9(S)-bromomethyl-octahydro-6,10-dioxo-6H-pyridazo[1,2-a][1,2]diazepine-1(S)-carboxylate was dissolved in 3 ml of trimethylphosphite and the solution was heated at reflux for 20 hours. Excess trimethylphosphite was removed in vacuo and the residue was chromatographed on silica gel using methanol/ethyl acetate for the elution. There were obtained 720 mg of methyl 9(S)-dimethoxyphosphinylmethyl-octahydro-6,10-dioxo-6H-pyridazo[1,2-a][1,2]diazepine-1(S)-carboxylate in the form of a pale yellow oil.

The methyl 9(S)-bromomethyl-octahydro-6,10-dioxo-6H-pyridazo[1,2-a][1,2]diazepine-1(S)-carboxylate used as the starting material was prepared as follows:

A solution of 10 g (0.0313 mol) of 1-benzyloxycarbonyl-S-piperazic acid tert.butyl ester in 100 ml of methanol was hydrogenated at room temperature and atmospheric pressure over 5% palladium/carbon. The catalyst was removed by filtration and the filtrate was evaporated to dryness. The resulting crude piperazic acid tert.butyl ester was taken up in 100 ml of dioxan, and the solution was cooled to 0° C. and treated with a solution of 3.94 g (0.0313 mol) of α-methylene-glutaric anhydride in 100 ml of dioxan. The mixture was stirred at 20° C. for 18 hours and the solvent was removed by evaporation. The residue was partitioned between methyl tert.butyl ether and saturated sodium bicarbonate solution. The aqueous phase was acidified with hydrochloric acid and extracted with dichloromethane to give 8.34 g (85%) of 3(S)-tert.butoxycarbonyl-hexahydro-α-methylene-δ-oxo-1-pyridazinepentanoic acid in the form of white crystals of melting point 96°–99° C. 5.0 g (16 mmol) of this acid were taken up in 350 ml of tetrahydrofuran and the solution was cooled to 0° C. 3.75 g (18 mmol) of phosphorus pentachloride were added and the mixture was stirred at 0° C. for 1 hour and at 20° C. for 18 hours. The solvent was removed by evaporation and the residue was partitioned between ethyl acetate and saturated sodium bicarbonate solution. The organic phase was evaporated and the residue was chromatographed on silica gel using ethyl acetate/n-hexane for the elution. There were obtained 3.7 g (79%) of tert.butyl octahydro-9-methylene-6,10-dioxo-6H-pyridazo[1,2-a][1,2]diazepine-1(S)-carboxylate as a white solid of melting point 105°–106° C. (from hexane).

10 g of tert.butyl octahydro-9-methylene-6,10-dioxo-6H-pyridazo[1,2-a][1,2]diazepine-1(S)-carboxylate were stirred with 40 ml of trifluoroacetic acid at 20° C. for 3 hours. The mixture was evaporated and the oil obtained was treated with diethyl ether to give 7.6 g of octahydro-9-methylene-6,10-dioxo-6H-pyridazo[1,2-a][1,2]diazepine-(S)-carboxylic acid in the form of a white solid of melting point 169°–172° C.

7.6 g of octahydro-9-methylene-6,10-dioxo-6H-pyridazo[1,2-a][1,2]diazepine-1(S)-carboxylic acid were suspended in 200 ml of ethyl acetate and the suspension was stirred at 0° C. during the addition of 100 ml of ethereal diazomethane solution. After 30 minutes excess diazomethane was destroyed by the dropwise addition of acetic acid. The mixture was washed with aqueous sodium bicarbonate solution, dried over sodium sulphate and evaporated to give 5.17 g of methyl octahydro-9-methylene-6,10-dioxo-6H-pyridazo[1,2-a][1,2]diazepine-1(S)-carboxylate in the form of a white solid of melting point 73°–75° C. (from n-hexane).

Hydrogen bromide was passed into a stirred solution of 5 g of methyl octahydro-9-methylene-6,10-dioxo-6H-pyridazo[1,2-a][1,2]diazepine-1(S)-carboxylate in 125 ml of dichloromethane during 4 hours at 20° C. The mixture was washed with saturated aqueous sodium bicarbonate solution, dried and evaporated. The residue was chromatographed on silica gel using ethyl acetate/n-hexane for the elution. There were obtained 5.03 g of methyl 9(S)-bromomethyl-octahydro-6,10-dioxo-6H-pyridazo[1,2-a][1,2]diazepine-1(S)-carboxylate in the form of a white solid of melting point 82°–83° C. (from ethyl acetate/n-hexane).

EXAMPLE 2

700 mg of methyl 9(S)-dimethoxyphosphinylmethyl-octahydro-6,10-dioxo-6H-pyridazo[1,2-a][1,2]diazepine-1(S)-carboxylate were dissolved in 15 ml of dry tetrahydrofuran and the solution was stirred at 0° C. under a nitrogen atmosphere during the dropwise addition over a period of 5 minutes of 4 ml of a 0.5 molar solution of borane in tetrahydrofuran. The stirring was continued for 30 minutes at 0° C. and for a further 3 hours at room temperature. The mixture was diluted with 75 ml of dichloromethane and cooled while 40 ml of 2N hydrochloric acid were added carefully. The stirring was continued for a further 30 minutes, the mixture was adjusted to pH 9 with sodium carbonate and the phases were separated. The aqueous phase was washed with dichloromethane and the combined organic extracts were dried over anhydrous sodium sulphate and evaporated. The residue was chromatographed on silica gel using methanol/ethyl acetate for the elution. There were obtained 510 mg of methyl 9(S)-dimethoxyphosphinylmethyl-octahydro-10-oxo-6H-pyridazo[1,2-a][1,2]diazepine-1(S)-carboxylate in the form of a colourless oil.

EXAMPLE 3

470 mg of methyl 9(S)-dimethoxyphosphinylmethyl-octahydro-10-oxo-6H-pyridazo[1,2-a][1,2]diazepine-1(S)-carboxylate were treated with 2 ml of trimethylsilyl bromide at room temperature for 17 hours. After evaporation the residue was taken up in acetone and water was added. Evaporation gave 490 mg of methyl octahydro-9(S)-phosphonomethyl-10-oxo-6H-pyridazo[1,2-a][1,2]diazepine-1(S)-carboxylate hydrobromide in the form of a wax-like solid.

EXAMPLE 4

450 mg of methyl octahydro-9(S)-phosphonomethyl-10-oxo-6H-pyridazo[1,2-a][1,2]diazepine-1(S)-carboxylate hydrobromide were taken up in 6 ml of water containing 350 mg of sodium hydroxide and the mixture was left to stand at 20° C. for 4 hours. The solution was washed with dichloromethane, the aqueous phase was diluted with an equal volume of methanol and applied to a column of Amberlite CG 120 resin [a strongly acidic cross-linked polystyrene-divinylbenzene cation exchange resin containing —$SO_3^-$ groups. Elution with aqueous methanol and evaporation of the eluate gave 360 mg of octahydro-9(S)-phosphonomethyl-10-oxo-6H-pyridazo[1,2-a][1,2]diazepine-1(S)-carboxylic acid hydrobromide in the form of an amorphous powder after trituration with diethyl ether.

EXAMPLE 5

515 mg of methyl 9(S)-bromomethyl-octahydro-6,10-dioxo-6H-pyridazo[1,2-a][1,2]diazepine-1(S)-carboxylate were dissolved in 1.5 ml of diethoxy-methylphosphine and the solution was heated at 120° C. under a nitrogen atmosphere for 7 hours. After evaporation the residue was chromatographed on silica gel using ethyl acetate for the elution. There were obtained 480 mg of methyl 9(S)-[[(ethoxy)methylphosphinyl]methyl]-octahydro-6,10-dioxo-6H-pyridazo-[1,2-a][1,2]diazepine-1(S)-carboxylate in the form of a colourless gum.

EXAMPLE 6

470 mg of methyl 9(S)-[[(ethoxy)methylphosphinyl]-methyl]-octahydro-6,10-dioxo-6H-pyridazo[1,2-a][1,2]diazepine-1(S)-carboxylate were stirred at 20° C. with 2 ml of trimethylsilyl bromide for 17 hours. After evaporation the residue was taken up in acetone, treated with water and re-evaporated. The residue was taken up in 6 ml of water containing 350 mg of sodium hydroxide and the solution was left to stand at 20° C. for 3 hours and subsequently washed with dichloromethane. The aqueous layer was diluted with an equal volume of methanol and applied to a column of Amberlite CG 120 resin. Elution with aqueous methanol gave 250 mg of octahydro-9(S)-[[(hydroxy)methylphosphinyl]methyl]-6,10-dioxo-6H-pyridazo[1,2-a][1,2]diazepine-1(S)-carboxylic acid in the form of a white lyophilizate.

EXAMPLE 7

2.5 g of methyl 9(RS)-bromo-octahydro-6,10-dioxo-6H-pyridazo[1,2-a][1,2]diazepine-1(S)-carboxylate were heated under reflux with 15 ml of triethylphosphite for 12 hours. Evaporation followed by chromatography on silica gel using methanol/ethyl acetate for the elution gave 1.4 g of methyl 9(S)-diethoxyphosphinyl-octahydro-6,10-dioxo-6H-pyridazo[1,2-a][1,2]diazepine-1(S)-carboxylate in the form of a pale yellow oil.

EXAMPLE 8

330 mg of methyl 9(S)-diethoxyphosphinyl-octahydro-6,10-dioxo-6H-pyridazo[1,2-a][1,2]diazepine-1(S)-carboxylate were treated with 2 ml of trimethylsilyl bromide and the mixture was stirred at 20° C. for 17 hours. The solution was evaporated to dryness and the residue was taken up in acetone and treated with water. After evaporation the residue was dissolved in 5 ml of water containing 200 mg of sodium hydroxide and the solution was left to stand at 20° C. for 4 hours. After washing with dichloromethane the aqueous phase was applied to a column of Amberlite CG 120 resin which was then eluted with water. The eluate was evaporated and the residue was triturated with diethyl ether to give 110 mg of octahydro-9(S)-phosphono-6,10-dioxo-6H-pyridazo[1,2-a][1,2]diazepine-1(S)-carboxylic acid in the form of an amorphous powder.

EXAMPLE 9

2.8 g of methyl 9(S)-diethoxyphosphinyl-octahydro-6,10-dioxo-6H-pyridazo[1,2-a][1,2]diazepine-1(S)-carboxylate were dissolved in 40 ml of ethanol and the solution was treated with a solution of 305 mg of sodium hydroxide in 10 ml of water. After 30 minutes at 20° C. the solution was evaporated. The residue was taken up in brine, washed with diethyl ether, acidified with 2N hydrochloric acid and extracted with dichloromethane. The dichloromethane extracts were dried over anhydrous sodium sulphate and evaporated. The residue was crystallized from ethanol/diethyl ether/n-hexane to give 1.4 g of 9(S)-diethoxyphosphinyl-octahydro-6,10-dioxo-6H-pyridazo[1,2-a][1,2]diazepine-1(S)-carboxylic acid in the form of a white solid of melting point 187°–189° C. (decomposition).

EXAMPLE 10

700 mg of methyl 9(S)-dimethoxyphosphinylmethyl-octahydro-6,10-dioxo-6H-pyridazo[1,2-a][1,2]diazepine-1(S)-carboxylate were dissolved in 10 ml of 2-butanone and 320 mg of lithium thiocyanate monohydrate were added. The mixture was heated under reflux for 24 hours and then evaporated. The residue was dissolved in 5 ml of methanol and 3.9 ml of 1N sodium hydroxide solution were added. After 5 minutes at 20° C. the solution was applied to a column of Amberlite GC 120 resin. Elution with aqueous methanol gave 620 mg of octahydro-9(S)-[[hydroxy(methoxy)phosphinyl]methyl]-6,10-dioxo-6H-pyridazo[1,2-a][1,2]diazepine-1(S)-carboxylic acid in the form of a white solid of melting point 80° C. (decomposition) (after trituration with diethyl ether).

Analysis for $C_{12}H_{19}N_2O_7P$:

Calculated: C, 43.12; H, 5.73; N, 8.38% Found(water-free): C, 43.31; H, 5.57; N, 8.20%.

EXAMPLE 11

In a manner analogous to that described in Example 1, from 500 mg of methyl 9(S)-bromomethyl-octahydro-6,10-dioxo-6H-pyridazo[1,2-a][1,2]diazepine-1(S)-carboxylate and 1 ml of triethylphosphite there were obtained 300 mg of methyl 9(S)-diethoxyphosphinyl-methyl-octahydro-6,10-dioxo-6H-pyridazo[1,2-a][1,2]diazepine-1(S)-carboxylate which was isolated in the form of a colourless gum.

NMR: $\delta(CDCl_3, 300 \text{ MHz})$ 5.45 (1H, m); 4.6 (1H, m); 4.1 (4H, m); 3.8 (3H, s); 3.4 (1H, m); 3.1 (1H, m); 2.85 (1H, m); 2.25–2.55 (4H, m), 1.6–2.0 (5H, m); 1.3 (6H, m).

EXAMPLE 12

In a manner analogous to that described in Example 8, from 300 mg of methyl 9(S)-diethoxyphosphinyl-methyl-octahydro-6,10-dioxo-6H-pyridazo[1,2-a][1,2]diazepine-1(S)-carboxylate there were obtained 250 mg of octahydro-9(S)-phosphonomethyl-6,10-dioxo-6H-pyridazo[1,2-a][1,2]diazepine-1(S)-carboxylic acid in the form of a white lyophilizate.

EXAMPLE 13

In a manner analogous to that described in Example 5, from 200 mg of methyl 9(S)-bromomethyl-octahydro-6,10-dioxo-6H-pyridazo[1,2-a][1,2]diazepine-1(S)-carboxylate and 700 mg of diethoxy-(3-phenylpropyl)-phosphine there were obtained 110 mg of methyl 9(S)-[[ethoxy(3-phenylpropyl)phosphinyl]methyl]-octahydro-6,10-dioxo-6H-pyridazo[1,2-a][1,2]diazepine-1(S)-carboxylate in the form of a colourless gum.

EXAMPLE 14

100 mg of methyl 9(S)-[ethoxy(3-phenylpropyl)phosphinyl]methyl-octahydro-6,10-dioxo-6H-pyridazo[1,2-a][1,2]diazepine-1(S)-carboxylate were dissolved in 1 ml of methanol and the solution was treated with 1 ml of water containing 50 mg of sodium hydroxide. The solution was left to stand at 20 C. for 5 hours and then applied to a column of Amberlite CG 120 resin. Elution with aqueous methanol and evaporation of the eluate gave a gum which was dissolved in 1 ml of acetonitrile. 0.5 ml of trimethylsilyl bromide were added to the solution which was then stirred at 20° C. for 17 hours and evaporated. The residue was dissolved in acetone and treated with water. Evaporation gave 60 mg of 9(S)-[[hydroxy(3-phenylpropyl)phosphinyl]methyl]-octahydro-6,10-dioxo-6H-pyridazo[1,2-a][1,2]diazepine-1(S)-carboxylic acid in the form of a pale yellow foam.

EXAMPLE 15

1.2 g of benzyl 9(S)-amino-octahydro-10-oxo-6H-pyridazo[1,2-a][1,2]diazepine-1(S)-carboxylate were dissolved in 25 ml of dichloromethane. 0.56 ml of triethylamine was added followed by a solution of 0.79 g of benzyl phenethylphosphochloridate in 5 ml of dichloromethane. The mixture was stirred at 20° C. for 4 hours, washed with water, dried over anhydrous sodium sulphate and evaporated. The residue was chromatographed on silica gel using ethyl acetate/n-hexane for the elution. There were obtained 550 mg of benzyl 9(S)-[[benzyloxy(phenethyl)phosphinyl]amino]-octahydro-10-oxo-6H-pyridazo[1,2-a][1,2]diazepine-1(S)-carboxylate in the form of a pale yellow gum.

EXAMPLE 16

250 mg of benzyl 9(S)-[[benzyloxy(phenethyl)phosphinyl]amino]-octahydro-10-oxo-6H-pyridazo[1,2-a][1,2]diazepine-1(S)-carboxylate and 73 mg of sodium hydrogen carbonate were dissolved in 100 ml of 25% aqueous ethanol and the mixture was hydrogenated over 10% palladium-on-carbon at atmospheric pressure for 17 hours. The catalyst was removed by filtration and the filtrate was evaporated. The residue was taken up in water and freeze-dried to give 145 mg of 9(S)-[[hydroxy(phenethyl)phosphinyl]amino]-octahydro-10-oxo-6H-pyridazo[1,2-a][1,2]diazepine-1(S)-carboxylic acid disodium salt in the form of a white lyophilizate.

EXAMPLE 17

30 mg of 80% sodium hydride was added to a stirred solution of 298 mg of tert.butyl octahydro-9(S)-hydroxy-6,10-dioxo-6H-pyridazo[1,2-a][1,2]diazepine-1(S)-carboxylate in 4 ml of tetrahydrofuran and the mixture was stirred at room temperature for 5 minutes. A solution of 297 mg of dibenzyl chlorophosphonate in 3 ml of carbon tetrachloride was added, the mixture was stirred at room temperature for 1 hour and the solvents were then removed by evaporation. The residue was chromatographed on silica gel using diethyl ether/methanol (19:1) for the elution to give 95 mg of tert.butyl 9(S)-(dibenzylphosphonoxy)octahydro-6,10-dioxo-6H-pyridazo[1,2-a][1,2]diazepine-1(S)-carboxylate in the form of a pale yellow gum.

The tert.butyl octahydro-9(S)-hydroxy-6,10-dioxo-6H-pyridazo[1,2-a][1,2]diazepine-1(S)-carboxylate used as the starting material can be prepared as follows:

9.6 g of 1-benzyl 3-tert.butyl hexahydropyridazine-1,3(S)-dicarboxylate were stirred at 8°-10° C. with 50 ml of toluene and 70 ml of 10% aqueous sodium bicarbonate solution during the addition of a solution in 45 ml of toluene of the acid chloride formed from 89.1 g of 2-acetoxy-4-benzyloxycarbonylbutanoic acid. The mixture was stirred at room temperature for 1 hour and the organic layer was separated. Chromatography on Florisil using toluene for the elution gave 15.3 g of 1-benzyl 3-tert.butyl 2-[2(S)-acetoxy-4-(benzyloxycarbonyl)-butyryl]-hexahydro-1,3(S)-pyridazine dicarboxylate in the form of a colourless gum.

14.5 g of 1-benzyl 3-tert.butyl 2-[2(S)-acetoxy-4-(benzyloxycarbonyl)butyryl]-hexahydro-1,3(S)-pyridazinedicarboxylate in 150 ml of dimethylformamide was hydrogenated over 0.5 g of 10% palladium-on-carbon at room temperature and atmospheric pressure. The catalyst was removed by filtration and the solvents were then removed by evaporation. The residue was taken up in 150 ml of dichloromethane and the solution was cooled and stirred under a slow stream of nitrogen during the addition of 2.97 g of thionyl chloride. The solution was stirred at room temperature for 2 hours and then washed with 10% aqueous potassium bicarbonate solution and saturated sodium chloride solution, dried over magnesium sulphate and evaporated. The residue was chromatographed on silica gel using diethyl ether/ethyl acetate (1:1) for the elution. There were obtained 5.7 g of tert.butyl 9(S)-acetoxy-octahydro-6,10-dioxo-6H-pyridazo[1,2-a][1,2]diazepine-1(S)-carboxylate in the form of a white solid of m.p. 80°-81° C. (from diethyl ether/n-hexane).

A solution of 0.68 g of tert.butyl 9(S)-acetoxy-octahydro-6,10-dioxo-6H-pyridazo[1,2-a][1,2]diazepine-1(S)-carboxylate in 5 ml of ethanol was treated with 10 ml of 0.4N aqueous sodium hydroxide solution at room temperature for 1 hour. The solvent was removed by evaporation and the residue was partitioned between water and dichloromethane. The organic phase was separated and evaporated to give 0.52 g of tert.butyl octahydro-9(S)-hydroxy-6,10-dioxo-6H-pyridazo[1,2-a][1,2]diazepine-1(S)-carboxylate in the form of a white solid of melting point 137°-138° C. (from diethyl ether).

EXAMPLE 18

0.15 g of 80% sodium hydride was added to a stirred solution of 1.49 g of tert.butyl octahydro-9(S)-hydroxy-6,10-dioxo-6H-pyridazo[1,2-a][1,2]diazepine-1(S)-carboxylate in 20 ml of tetrahydrofuran and the mixture was stirred at room temperature for 5 minutes. A solution of 1.47 g of benzyl phenethylphosphochloridate in 10 ml of tetrahydrofuran was added, the mixture was stirred at room temperature for 1 hour and the solvents were then removed by evaporation. The residue was chromatographed on silica gel using diethyl ether/methanol (19:1) for the elution. There were obtained 1.44 g of tert.butyl 9(S)-[benzyloxy(phenethyl)phosphinyloxy]-octahydro-6,10-dioxo-6H-pyridazo[1,2-a][1,2]diazepine-1(S)-carboxylate in the form of a colourless gum.

EXAMPLE 19

0.1 g of triethylamine and 0.35 g of dibenzyl chlorophosphonate in 3.6 ml of carbon tetrachloride were added to a stirred solution, cooled to 0° C., of 0.32 g of benzyl 9(S)-amino-octahydro-10-oxo-6H-pyridazo[1,2-a][1,2]diazepine-1(S)-carboxylate in 5 ml of dichloromethane. The mixture was stirred at room temperature for 16 hours and the solvents were then removed by evaporation. The residue was chromatographed on silica gel using ethyl acetate/n-hexane (2:1) for the elution. There was obtained 0.25 g of benzyl 9(S)-[(dibenzyloxyphosphinyl)amino]-octahydro-10-oxo-6H-pyridazo[1,2-a][1,2]diazepine-1(S)-carboxylate in the form of a colourless gum.

EXAMPLE 20

A solution of 1.88 g of benzyl 9(S)-[(dibenzyloxyphosphinyl)amino]-octahydro-10-oxo-6H-pyridazo[1,2-a][1,2]diazepine-1(S)-carboxylate in 20 ml of methanol was treated with 4.9 ml of 1N aqueous sodium hydroxide solution at room temperature for 16 hours. The solution was diluted with 50 ml of water and the volume was then reduced to 20 ml. The pH was adjusted to 3.5 and the solution was extracted with dichloromethane. The organic solution was evaporated and the residue was chromatographed on silica gel to give 1.42 g of 9(S)-[(dibenzyloxyphosphinyl)amino]-octahydro-10-oxo-6H-pyridazo[1,2-a][1,2]diazepine-1(S)-carboxylic acid in the form of a lyophilizate (from benzene).

EXAMPLE 21

In a manner analogous to that described in Example 18, from 1.1 g of tert.butyl octahydro-9(S)-hydroxy-6,10-dioxo-6H-pyridazo[1,2-a][1,2]diazepine-1(S)-carboxylate and 1.21 g of benzyl 4-phenylbutylphosphochloridate there was obtained 0.90 g of tert.butyl 9(S)-[benzyloxy(4-phenylbutyl)phosphinyloxy]-octahydro-6,10-dioxo-6H-pyridazo[1,2-a][1,2]diazepine-1(S)-carboxylate in the form of a colourless gum.

EXAMPLE 22

A solution of 0.4 g of tert.butyl 9(S)-[benzyloxy(4-phenylbutyl)phosphinyloxy]-octahydro-6,10-dioxo-6H- pyridazo[1,2-a][1,2]diazepine-1(S)-carboxylate in 40 ml of isopropanol was hydrogenated over 10% palladium-on-carbon at atmospheric pressure for 16 hours. The catalyst was removed by filtration and the filtrate was evaporated. The resulting gum was dissolved in 10 ml of trifluoroacetic acid, the solution was left to stand at 20° C. for 1 hour and then evaporated to give 0.24 g of 9(S)-[hydroxy(4-phenylbutyl)phosphinyloxy]-octahydro-6,10-dioxo-6H-pyridazo[1,2-a][1,2]diazepine-1(S)-carboxylate acid in the form of a colourless gum.

EXAMPLE 23

In a manner analogous to that described in Example 15, from 0.8 g of benzyl 9(S)-amino-octahydro-10-oxo-6H-pyridazo[1,2-a][1,2]diazepine-1(S)-carboxylate and 0.49 g of benzyl benzylphosphochloridate there was obtained 0.127 g of benzyl 9(S)-[[benzyloxy(benzyl)-phosphinyl]amino]-octahydro-10-oxo-6H-pyridazo[1,2-a][1,2]diazepine-1(S)-carboxylate in the form of a colourless gum.

EXAMPLE 24

In a manner analogous to that described in Example 15, from 1.15 g of benzyl 9(S)-amino-octahydro-10-oxo-6H-pyridazo[1,2-a][1,2]diazepine-1(S)-carboxylate and 0.73 g of benzyl 3-phenylpropylphosphochloridate there was obtained 0.31 g of benzyl 9(S)-[[benzyloxy(3-phenylpropyl)phosphinyl]amino]-octahydro-10-oxo-6H-pyridazo[1,2-a][1,2]diazepine-1(S)-carboxylate in the form of a colourless gum.

EXAMPLE 25

In a manner analogous to that described in Example 15, from 1.13 g of benzyl 9(S)-amino-octahydro-10-oxo-6H-pyridazo[1,2-a][1,2]diazepine-1(S)-carboxylate and 0.83 g of benzyl 4-phenylbutylphosphochloridate there was obtained 0.33 g of benzyl 9(S)-[[benzyloxy(4-phenylbutyl)phosphinyl]amino]-octahydro-10-oxo-6H-pyridazo[1,2-a][1,2]diazepine-1(S)-carboxylate in the form of a colourless gum.

EXAMPLE 26

In a manner analogous to that described in Example 16, from 260 mg of benzyl 9(S)-[[benzyloxy(benzyl)-phosphinyl]amino]-octahydro-10-oxo-6H-pyridazo[1,2-a][1,2]diazepine-1(S)-carboxylate there were obtained 190 mg of 9(S)-[[hydroxy(benzyl)phosphinyl]amino]-octahydro-10-oxo-6H-pyridazo[1,2-a][1,2]diazepine-1(S)-carboxylic acid disodium salt in the form of a white lyophilizate.

EXAMPLE 27

In a manner analogous to that described in Example 16, from 290 mg of benzyl 9(S)-[[benzyloxy(3-phenylpropyl)phosphinyl]amino]-octahydro-10-oxo-6H-pyridazo[1,2-a][1,2]diazepine-1(S)-carboxylate there were obtained 230 mg of 9(S)-[[hydroxy(3-phenylpropyl)phosphinyl]amino]-octahydro-10-oxo-6H-pyridazo[1,2-a][1,2]diazepine-1(S)-carboxylic acid disodium salt in the form of a white lyophilizate.

EXAMPLE 28

In a manner analogous to that described in Example 16, from 280 mg of benzyl 9(S)-[[benzyloxy(4-phenylbutyl)phosphinyl]amino]-octahydro-10-oxo-6H-pyridazo[1,2-a][1,2]diazepine-1(S)-carboxylate there were obtained 200 mg of 9(S)-[[hydroxy(4-phenylbutyl)phosphinyl]amino]-octahydro-10-oxo-6H-pyridazo[1,2-a][1,2]diazepine-1(S)-carboxylic acid disodium salt in the form of a white lyophilizate.

EXAMPLE 29

3 g of methyl 9(RS)-bromo-octahydro-6,10-dioxo-6H-pyridazo[1,2-a][1,2]diazepine-1(S)-carboxylate and 8.1 g of diethyl 5-phenylpentylphosphonite were heated together at 150° C. for 12 hours. Evaporation followed by chromatography on silica gel using methanol/ethyl acetate for the elution gave 1.3 g of methyl 9(S)-[(ethoxy)(5-phenylpentyl)phosphinyl]-octahydro-6,10-dioxo-6H-pyridazo[1,2-a][1,2]diazepine-1(S)-carboxylate in the form of a colourless gum.

EXAMPLE 30

In a manner analogous to that described in Example 29, from 1 g of methyl 9(RS)-bromo-octahydro-6,10-dioxo-6H-pyridazo[1,2-a][1,2]diazepine-1(S)-carboxylate and 3 g of diethyl 4-phenylbutylphosphonite there were obtained 350 mg of methyl 9(S)-[(ethoxy)(4-phenylbutyl)phosphinyl]-octahydro-6,10-dioxo-6H-pyridazo[1,2-a][1,2]diazepine-1(S)-carboxylate in the form of a gum.

EXAMPLE 31

In a manner analogous to that described in Example 29, from 1 g of methyl 9(RS)-bromo-octahydro-6,10-dioxo-6H-pyridazo[1,2-a][1,2]diazepine-1(S)-carboxylate and 2.25 g of diethyl 3-phenylpropylphosphonite there were obtained 220 mg of methyl 9(S)-[(ethoxy)(3-phenylpropyl)phosphinyl]-octahydro-6,10-dioxo-6H-pyridazo[1,2-a][1,2]diazepine-1(S)-carboxylate in the form of a gum.

EXAMPLE 32

In a manner analogous to that described in Example 29, from 1 g of methyl 9(RS)-bromo-octahydro-6,10-dioxo-6H-pyridazo[1,2-a][1,2]diazepine-1(S)-carboxylate and 2.6 g of diethyl 2-phenethylphosphonite there were obtained 410 mg of methyl 9(S)-[(ethoxy)(phenethyl)phosphinyl]-octahydro-6,10-dioxo-6H-pyridazo[1,2-a][1,2]diazepine-1(S)-carboxylate in the form of a gum.

EXAMPLE 33

1.2 g of methyl 9(S)-[(ethoxy)(5-phenylpentyl)phosphinyl]-octahydro-6,10-dioxo-6H-pyridazo[1,2-][1,2]diazepine-1(S)-carboxylate were treated with a solution of 1 g of sodium hydroxide in 15 ml of water and the mixture was stirred at 20° C. for 24 hours. The mixture was placed on a sulphonic acid ion-exchange resin and eluted with 50% methanol/water. The eluate was evaporated and the residue was chromatographed on silica gel using chloroform/methanol/acetic acid/water (120:14:3:2) for the elution. The product was dissolved in 20 ml of acetonitrile and the solution was treated with 5 ml of trimethylsilyl bromide. The solution was stirred at 20° C. for 17 hours and then evaporated. The residue was dissolved in 30 ml of acetone and 20 ml of water were added. After 2 hours the mixture was evaporated and the residue was treated with diethyl ether to give 520 mg of 9(S)-[hydroxy(5-phenylpentyl)phosphinyl]-octahydro-6,10-dioxo-6H-pyridazo[1,2-a][1,2]diazepine-1(S)-carboxylic acid in the form of a white solid of melting point 218°-220° C. (from methanol).

EXAMPLE 34

In a manner analogous to that described in Example 6, from 300 mg of methyl 9(S)-[(ethoxy)(4-phenylbutyl)phosphinyl]-octahydro-6,10-dioxo-6H-pyridazo[1,2-a][1,2]diazepine-1(S)-carboxylate there were obtained 150 mg of 9(S)-[hydroxy(4-phenylbutyl)phosphinyl]-octahydro-6,10-dioxo-6H-pyridazo[1,2-a][1,2]diazepine-1(S)-carboxylic acid in the form of a white lyophilizate.

EXAMPLE 35

In a manner analogous to that described in Example 6, from 210 mg of methyl 9(S)-[(ethoxy)(3-phenylpropyl)phosphinyl]-octahydro-6,10-dioxo-6H-pyridazo[1,2-a][1,2]diazepine-1(S)-carboxylate there were obtained 80 mg of 9(S)-[hydroxy(3-phenylpropyl)phosphinyl]-octahydro-6,10-dioxo-6H-pyridazo[1,2-a][1,2]diazepine-1(S)-carboxylic acid in the form of an amorphous white solid.

EXAMPLE 36

In a manner analogous to that described in Example 33, from 340 mg of methyl 9(S)-[(ethoxy)(phenethyl)phosphinyl]-octahydro-6,10-dioxo-6H-pyridazo[1,2-a][1,2]diazepine-1(S)-carboxylate there were obtained 100 mg of 9(S)-[hydroxy(phenethyl)phosphinyl]-octahydro-6,10-dioxo-6H-pyridazo[1,2-a][1,2]diazepine-1(S)-carboxylic acid in the form of a tan coloured lyophilizate.

EXAMPLE 37

In a manner analogous to that described in Example 5, from 1 g of methyl 9(S)-bromomethyl-octahydro-6,10-dioxo-6H-pyridazo[1,2-a][1,2]diazepine-1(S)-carboxylate and 2 g of diethyl 2-phenethylphosphonite there were obtained 630 mg of methyl 9(S)-[[ethoxy(phenethyl)phosphinyl]methyl]octahydro-6,10-dioxo-6H-pyridazo[1,2-a][1,2]diazepine-1(S)-carboxylate in the form of a pale yellow gum.

EXAMPLE 38

In a manner analogous to that described in Example 6, from 630 mg of methyl 9(S)-[[ethoxy(phenethyl)phosphinyl]methyl]octahydro-6,10-dioxo-6H-pyridazo[1,2-a][1,2]diazepine-1(S)-carboxylate there were obtained 430 mg of 9(S)-[[hydroxy(phenethyl)phosphinyl]methyl]octahydro-6,10-dioxo-6H-pyridazo[1,2-a][1,2]diazepine-1(S)-carboxylic acid in the form of a white lylophilizate.

EXAMPLE 39

In a manner analogous to that described in Example 2, from 1.34 g of methyl 9(S)-[[ethoxy(phenethyl)phosphiny]methyl]octahydro-6,10-dioxo-6H-pyridazo[1,2-a][1,2]diazepine-1(S)-carboxylate there were obtained 350 mg of methyl 9(S)-[[ethoxy(phenethyl)phosphinyl]methyl]octahydro-10-oxo-6H-pyridazo[1,2-a][1,2]diazepine-1(S)-carboxylate in the form of a colourless oil.

EXAMPLE 40

In an manner analogous to that described in Example 6, from 330 mg of methyl 9(S)-[[ethoxy(2-phenethyl)phosphinyl]methyl]octahydro-10-oxo-6H-pyridazo[1,2-a][1,2]diazepine-1(S)-carboxylate there were obtained 240 mg of 9(S)-[[hydroxy(2-phenethyl)phosphinyl]methyl]octahydro-10-oxo-6H-pyridazo[1,2-a][1,2]diazepine-1(S)-carboxylic acid in the form of a pale yellow lyophilizate from acetic acid.

EXAMPLE 41

In a manner analogous to that described in Example 2, from 2.5 g of methyl 9(S)-[(ethoxy)(4-phenylbutyl)phosphinyl]-octahydro-6,10-dioxo-6H-pyridazo[1,2-a][1,2]diazepine-1(S)-carboxylate there were obtained 820 mg of methyl 9(S)-[(ethoxy)(4-phenylbutyl)phosphinyl]-octahydro-10-oxo-6H-pyridazo[1,2-a][1,2]diazepine-1(S)-carboxylate in the form of a pale yellow viscous oil.

EXAMPLE 42

In a manner analogous to that described in Example 6, from 670 mg of methyl 9(S)-[(ethoxy)(4-phenylbutyl)phosphinyl]-octahydro-10-oxo-6H-pyridazo[1,2-a][1,2]diazepine-1(S)-carboxylate there were obtained 270 mg of 9(S)-[(hydroxy)(4-phenylbutyl)phosphinyl]-octahydro-10-oxo-6H-pyridazo[1,2-a][1,2]diazepine-1(S)-carboxylic acid dipotassium salt in the form of a white lyophilizate.

EXAMPLE 43

A mixture of 1.2 g of 9-methylene-octahydro-6,10-dioxo-6H-pyridazo[1,2-a][1,2]diazepine-1(S)-carboxylic acid and 4.3 g of diethyl 4-benzyloxybutyphosphonite in 25 ml of xylene was heated at 110° C. under nitrogen for 24 hours. The solvent was removed in vacuo and the residue was chromatographed on silica gel using 5% methanol in ethyl acetate for the elution. There were obtained 2.0 g of ethyl 9(S)-[[(4-benzyloxybutyl)(ethoxy)phosphinyl]methyl]-octahydro-6,10-dioxo-6H-pyridazo[1,2-a][1,2]diazepine-1(S)-carboxylate in the form of a viscous oil.

The 9-methylene-octahydro-6,10-dioxo-6H-pyridazo[1,2-a][1,2]diazepine-1(S)-carboxylic acid used as the starting material was prepared as follows:

10 g of tert.butyl octahydro-9-methylene-6,10-dioxo-6H-pyridazo[1,2-a][1,2]diazepine-1(S)-carboxylate, prepared as described in Example 48, were stirred with 40 ml of trifluoroacetic acid at 20° C. for 3 hours. The mixture was evaporated and the oil obtained was treated with diethyl ether to give 7.6 g of 9-methylene-octahydro-6,10-dioxo-6H-pyridazo[1,2-a][1,2]diazepine-(S)-carboxylic acid in the form of a white solid of melting point 169°–172° C.

EXAMPLE 44

In a manner analogous to that described in Example 6, from 700 mg of ethyl 9(S)-[[(4-benzyloxybutyl)(ethoxy)phosphinyl]methyl]-octahydro-6,10-dioxo-6H-pyridazo[1,2-a][1,2]diazepine-1(S)-carboxylate there were obtained 400 mg of 9(S)-[[(4-benzyloxybutyl)(hydroxy)phosphinyl]methyl]-octahydro-6,10-dioxo-6H-pyridazo[1,2-a][1,2]diazepine-1(S)-carboxylic acid in the form of a colourless gum.

EXAMPLE 45

275 mg of 9(S)-[[(4-benzyloxybutyl)(hydroxy)phosphinyl]methyl]-octahydro-6,10-dioxo-6H-pyridazo[1,2-a][1,2]diazepine-1(S)-carboxylic acid were dissolved in 30 ml of ethanol containing 3 ml of acetic acid and the solution was hydrogenated over 10% palladium-on-carbon for 16 hours. The catalyst was removed by filtration and the filtrate was evaporated. The residue was taken up in water and the pH was adjusted to 7 with potassium bicarbonate. Evaporation and treatment with acetone gave 190 mg of 9(S)-[[(4-hydroxybutyl)(hydroxy)phosphinyl]methyl]-octahydro-6,10-dioxo-6H-pyridazo[1,2-a][1,2]diazepine-1(S)-carboxylic acid dipotassium salt in the form of a white hygroscopic solid.

EXAMPLE 46

350 mg of ethyl 9(S)-[[(4-benzyloxybutyl)(ethoxy)phosphinyl]methyl]-octahydro-6,10-dioxo-6H-pyridazo[1,2-a][1,2]diazepine-1(S)-carboxylate were dissolved in a mixture of 20 ml of ethanol and 2 ml of acetic acid and the solution was hydrogenated over 10% palladium-on-carbon for 16 hours. The catalyst was removed by filtration and the filtrate was evaporated. The residue was taken up in 5 ml of dichloromethane and stirred at 20° C. while 0.18 ml of triethylamine and subsequently a solution of 0.075 ml of methanesulphonyl chloride in 4 ml of dichloromethane were added. Stirring was continued for 2 hours and the mixture was then washed successively with 2N hydrochloric acid, sodium bicarbonate solution and saturated sodium chloride solution. The organic phase was dried over anhydrous magnesium sulphate and evaporated. The residue was taken up in 20 ml of 2-butanone and 60 mg of sodium azide were added. The mixture was heated under reflux for 20 hours and then evaporated. The residue was partitioned between ethyl acetate and water. The organic layer was evaporated and the residue was chromatographed on silica gel using 10% methanol in ethyl acetate for the elution, there being obtained 130 mg of ethyl 9(S)-[[(4-azidobutyl)(ethoxy)phosphinyl]methyl]-octahydro-6,10-dioxo-6H-pyridazo[1,2-a][1,2]diazepine-1(S)-carboxylate in the form of a gum. This gum was taken up in 15 ml of ethanol and the solution was hydrogenated over 10% palladium-on-carbon for 3 hours. Filtration and evaporation of the filtrate gave 120 mg of ethyl 9(S)-[[(4-aminobutyl)(ethoxy)phosphinyl]methyl]-octahydro-6,10-dioxo-6H-pyridazo[1,2-a][1,2]diazepine-1(S)-carboxylate in the form of a gum.

EXAMPLE 47

In a manner analogous to that described in Example 6, from 120 mg of ethyl 9(S)-[[(4-aminobutyl)-(ethoxy)phosphinyl]methyl]-octahydro-6,10-dioxo-6H-pyridazo[1,2-a][1,2]diazepine-1(S)-carboxylate there were obtained 55 mg of 9(S)-[[(4-aminobutyl)(hydroxy)phosphinyl]methyl]-octahydro-6,10-dioxo-6H-pyridazo[1,2-a][1,2]diazepine-1(S)-carboxylic acid in the form of a pale yellow gum.

EXAMPLE 48

A solution of 2.8 g of 1-[2-(methoxyphosphinyl)ethyl]-4-nitrobenzene and 3.6 g of tert.butyl octahydro-9-methylene-6,10-dioxo-6H-pyridazo[1,2-a][1,2]diazepine-1(S)-carboxylate in 80 ml of toluene was treated under nitrogen with 2.49 g of N,O-bis(trimethylsilyl)acetamide. After heating at 60° C. for 65 hours the solution was diluted with 100 ml of dichloromethane, washed with water and evaporated. The residue was chromatographed on silica gel using 10% methanol in ethyl acetate for the elution and there was thus obtained 1.0 g of tert.butyl octahydro-9(S)-[[methoxy(4-nitrophenethyl)phosphinyl]methyl]-6,10-dioxo-6H-pyridazo[1,2-a][1,2]diazepine-1(S)-carboxylate in the form of a pale yellow foam.

The tert.butyl octahydro-9-methylene-6,10-dioxo-6H-pyridazo[1,2-a][1,2]diazepine-1(S)-carboxylate used as the starting material was prepared as described in Example 1, i.e. in the first paragraph of the procedure described for the preparation of the starting material used therein.

The 1-[2-(methoxyphosphinyl)ethyl]-4-nitrobenzene referred to in the first paragraph of this Example was prepared as follows:

0.665 g of crystalline hypophosphorous acid was treated under nitrogen with 1.73 g of trimethyl orthoformate and the mixture was stirred at 20° C. for 2 hours. The resulting solution of crude methyl hypophosphite was added dropwise at 0° C. to a solution of 1 g of 4-nitrostyrene and 0.43 g of diisopropylethylamine in 5 ml of methanol. After 65 hours at 20° C. the same amount of methyl hypophosphite was again added and the mixture was stirred at 20° C. for a further 24 hours. The mixture was diluted with 30 ml of water and the pH was adjusted to 7 with aqueous sodium bicarbonate solution. After extraction with dichloromethane and chromatography on silica gel using 10% methanol in ethyl acetate for the elution there was obtained 0.5 g of 1-[2-(methoxyphosphinyl)ethyl]-4-nitrobenzene in the form of a yellow liquid.

EXAMPLE 49

0.48 g of tert.butyl octahydro-9(S)-[[methoxy(4-nitrophenethyl)phosphinyl]methyl]-6,10-dioxo-6H-pyridazo[1,2-a][1,2]diazepine-1(S)-carboxylate was stirred in 2 ml of trifluoroacetic acid at 20° C. for 1 hour. The mixture was evaporated and the residue was partitioned between sodium bicarbonate solution and dichloromethane. The aqueous phase was acidified with 2N hydrochloric acid and then extracted with dichloromethane. Evaporation of the extract gave 0.29 g of octahydro-9(S)-[[methoxy(4-nitrophenethyl)phosphinyl]methyl]-6,10-dioxo-6H-pyridazo[1,2-a][1,2]diazepine-1(S)-carboxylic acid in the form of a white foam.

EXAMPLE 50

A solution of 0.1 g of octahydro-9(S)-[[methoxy(4-nitrophenethyl)phosphinyl]methyl]-6,10-dioxo-6H-pyridazo[1,2-a][1,2]diazepine-1(S)-carboxylic acid in 1 ml of acetonitrile was treated under nitrogen with 1 ml of trimethylsilyl bromide. The solution was stirred at 20° C. for 30 minutes and then evaporated. The residue was dissolved in aqueous acetone and the solution was stirred for 30 minutes and then evaporated. The residue was treated with diethyl ether to give 0.075 g of octahydro-9(S)-[[hydroxy(4-nitrophenethyl)phosphinyl]methyl]-6,10-dioxo-6H-pyridazo[1,2-a][1,2]diazepine-1(S)-carboxylic acid in the form of an amorphous solid.

EXAMPLE 51

0.12 g of octahydro-9(S)-[[hydroxy(4-nitrophenethyl)phosphinyl]methyl]-6,10-dioxo-6H-pyridazo[1,2-a][1,2]diazepine-1(S)-carboxylic acid in 50 ml of methanol was hydrogenated over 10% palladium-on-carbon for 5 hours. The catalyst was removed by filtration and the filtrate was evaporated. After treating the residue with diethyl ether there was obtained 0.1 g of 9(S)-[[(4-aminophenethyl)hydroxyphosphinyl]methyl]-octahydro-6,10-dioxo-6H-pyridazo[1,2-a][1,2]diazepine-1(S)-carboxylic acid in the form of an amorphous solid.

EXAMPLE 52

In a manner analogous to that described in Example 51, from 0.125 g of octahydro-9(S)-[[methoxy(4-nitrophenethyl)phosphinyl]methyl]-6,10-dioxo-6H- pyridazo[1,2-a][1,2]diazepine-1(S)-carboxylic acid there was obtained 0.112 g of 9(S)-[[(4-aminophenethyl)methoxyphosphinyl]methyl]-octahydro-6,10-dioxo-6H-pyridazo[1,2-a][1,2]diazepine-1(S)-carboxylic acid in the form of a gum.

EXAMPLE 53

0.11 g of 9(S)-[[(4-aminophenethyl)methoxyphosphinyl]methyl]-octahydro-6,10-dioxo-6H-pyridazo[1,2-a][1,2]diazepine-1(S)-carboxylic acid was dissolved in 3 ml of acetonitrile and 3 ml of trimethylsilyl bromide were added. The solution was stirred at 20° C. for 90 hours. Evaporation and treatment of the residue with aqueous acetone followed by re-evaporation gave, after preparative high pressure liquid chromatography, 0.025 g of octahydro 9(S)-[[(hydroxy)[4-(1-iminoethylamino)-phenethyl]phosphinyl]methyl]-6,10-dioxo-6H-pyridazo[1,2-a][1,2]diazepine-1(S)-carboxylic acid in the form of an amorphous solid.

The following Examples illustrate pharmaceutical preparations containing the compounds provided by the present invention:

EXAMPLE A

Tablets containing the following ingredients may be produced in a conventional manner:

| Ingredient | Per tablet |
| --- | --- |
| Compound of formula I | 10.0 mg |
| Lactose | 125.0 mg |
| Maize starch | 75.0 mg |
| Talc | 4.0 mg |
| Magnesium stearate | 1.0 mg |
| Tablet weight | 215.0 mg |

EXAMPLE B

Capsules containing the following ingredients may be produced in a conventional manner:

| Ingredient | Per capsule |
| --- | --- |
| Compound of formula I | 25.0 mg |
| Lactose | 150.0 mg |
| Maize starch | 20.0 mg |
| Talc | 5.0 mg |
| Capsule fill weight | 200.0 mg |

What is claimed is:
1. A compound of the formula

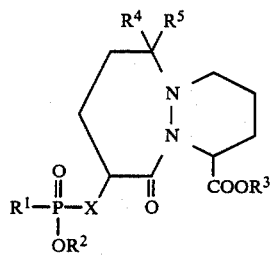

I wherein $R^1$ is hydroxy, alkyl, aralkyl, aralkoxy-alkyl, hydroxy-alkyl, amino-alkyl, acylamino-alkyl, monoalkylamino-alkyl, dialkylamino-alkyl, alkoxycarbonylamino-alkyl, halo-alkyl, carboxy-alkyl, alkoxycarbonyl-alkyl, alkoxy or aralkoxy; $R^2$ and $R^3$ each are hydrogen, alkyl or aralkyl; $R^4$ and $R^5$ each are hydrogen or $R^4$ and $R^5$ together are oxo; and X is oxygen, $-NR^6-$ or $-(CH_2)_n-$; $R^6$ is hydrogen, alkyl or aralkyl; and n is zero, 1 or 2,
and racemates, enantiomers, diastereoisomers or pharmaceutically acceptable salts thereof.

2. The compound of claim 1, wherein $R^1$ is hydroxy, alkyl, aralkyl or alkoxy.

3. The compound of to claim 1, wherein $R^2$ is hydrogen.

4. The compound of claim 1, wherein $R^3$ is hydrogen.

5. The compound of claim 1, wherein X is oxygen or $-NH-$ or $-(CH_2)_n-$ in which n is zero or 1.

6. The compound of claim 1, wherein $R^1$ is hydroxy, alkyl, aralkyl or alkoxy, $R^2$ is hydrogen, $R^3$ is hydrogen and X is oxygen, $-NH-$ or $-(CH_2)_n-$ in which n is zero or 1.

7. The compound of claim 1, octahydro-9(S)-phosphonomethyl-10-oxo-6H-pyridazo-[1,2-a][1,2]diazepine-1(S)-carboxylic acid.

8. The compound of claim 1, octahydro-9(S)-[[(hydroxy)methylphosphinyl]methyl]-6,10-dioxo-6H-pyridazo[1,2-a][1,2]diazepine-1(S)-carboxylic acid.

9. The compound of claim 1, octahydro-9(S)-phosphono-6,10-dioxo-6H-pyridazo[1,2-a][1,2]diazepine-1(S)-carboxylic acid.

10. The compound of claim 1, 9(S)-diethoxyphosphinyl-octahydro-6,10-dioxo-6H-pyridazo[1,2-a][1,2]diazepine-1(S)-carboxylic acid.

11. The compound of claim 1, octahydro-9(S)-[[hydroxy(methoxy)phosphinyl]methyl]-6,10-dioxo-6H-pyridazo[1,2-a][1,2]diazepine-1(S)-carboxylic acid.

12. The compound of claim 1, octahydro-9(S)-phosphonomethyl-6,10-dioxo-6H-pyridazo-[1,2-a][1,2]diazepine-1(S)-carboxylic acid.

13. The compound of claim 1, 9(S)-[[hydroxy(3-phenylpropyl)phosphinyl)]methyl]-octahydro-6,10-dioxo-6H-pyridazo[1,2-a][1,2]diazepine-1(S)-carboxylic acid.

14. The compound of claim 1, 9(S)-[[hydroxy(phenethyl)phosphinyl]amino]-octahydro-10-oxo-6H-pyridazo[1,2-a][1,2]diazepine-1(S)-carboxylic acid.

15. The compound of claim 1, 9(S)-[[hydroxy(2-phenethyl)phosphinyl]methyl]-octahydro-10-oxo-6H-pyridazo[1,2-a][1,2]diazepine-1(S)-carboxylic acid.

16. The compound of claim 1, 9(S)-[hydroxy(4-phenylbutyl)phosphinyl]-octahydro-10-oxo-6H-pyridazo[1,2-a][1,2]diazepine-1(S)-carboxylic acid.

17. The compound of claim 1, taken from the group consisting of:
methyl 9(S)-dimethoxyphosphinylmethyl-octahydro-6,10-dioxo-6H-pyridazo[1,2-a][1,2]diazepine-1(S)-carboxylate,
methyl 9(S)-dimethoxyphosphinylmethyl-octahydro-10-oxo-6H-pyridazo[1,2-a][1,2]diazepine-1(S)-carboxylate,
methyl octahydro-9(S)-phosphonomethyl-10-oxo-6H-pyridazo[1,2-a][1,2]diazepine-1(S)-carboxylate,
methyl 9(S)-[[(ethoxy)methylphosphinyl]methyl]-octahydro-6,10-dioxo-6H-pyridazo[1,2-a][1,2]diazepine-1(S)-carboxylate,
methyl 9(S)-diethoxyphosphinyl-octahydro-6,10-dioxo-6H-pyridazo[1,2-a][1,2]diazepine-1(S)-carboxylate,
methyl 9(S)-diethoxyphosphinylmethyl-octahydro-6,10-dioxo-6H-pyridazo[1,2-a][1,2]diazepine-1(S)-carboxylate, methyl 9(S)-[[ethoxy(3-phenylpropyl)phosphinyl]methyl]octahydro-6,10-dioxo-6H-pyridazo[1,2-a][1,2]diazepine-1(S)-carboxylate,
benzyl 9(S)-[[benzyloxy(phenethyl)phosphinyl]amino]-octahydro-10-oxo-6H-pyridazo[1,2-a][1,2]diazepine-1(S)-carboxylate,
tert.butyl 9(S)-(dibenzylphosphonoxy)-octahydro-6,10-dioxo-6H-pyridazo[1,2-a][1,2]diazepine-1(S)-carboxylate,
tert.butyl 9(S)-[benzyloxy(phenethyl)phosphinyloxy]-octahydro-6,10-dioxo-6H-pyridazo[1,2-a][1,2]diazepine-1(S)-carboxylate,
benzyl 9(S)-[(dibenzyloxyphosphinyl)amino]-octahydro-10-oxo-6H-pyridazo[1,2-a][1,2]diazepine-1(S)-carboxylate and
9(S)-[dibenzyloxyphosphinyl)amino]-octahydro-10-oxo-6H-pyridazo[1,2-a][1,2]diazepine-1(S)-carboxylic acid.

18. The compound of claim 1, taken from the group consisting of:
tert.butyl 9(S)-[benzyloxy(4-phenylbutyl)phosphinyloxy]-octahydro-6,10-dioxo-6H-pyridazo[1,2-a][1,2]diazepine-1(S)-carboxylate,
9(S)-[hydroxy(4-phenylbutyl)phosphinyloxy]-octahydro-6,10-dioxo-6H-pyridazo[1,2-a][1,2]diazepine-1(S)-carboxylic acid,
benzyl 9(S)-[[benzyloxy(benzyl)phosphinyl]amino]-octahydro-10-oxo-6H-pyridazo[1,2-a][1,2]diazepine-1(S)-carboxylate,
benzyl 9(S)-[[benzyloxy(3-phenylpropyl)phosphinyl]amino]-octahydro-10-oxo-6H-pyridazo[1,2-a][1,2]diazepine-1(S)-carboxylate,
benzyl 9(S)-[[benzyloxy(4-phenylbutyl)phosphinyl]amino]-octahydro-10-oxo-6H-pyridazo[1,2-a][1,2]diazepine-1(S)-carboxylate,
9(S)-[[hydroxy(benzyl)phosphinyl]amino]-octahydro-10-oxo-6H-pyridazo[1,2-a][1,2]diazepine-1(S)-carboxylic acid,
9(S)-[[hydroxy(3-phenylpropyl)phosphinyl]amino]octahydro-10-oxo-6H-pyridazo[1,2-a][1,2]diazepine-1(S)-carboxylic acid,
9(S)-[[hydroxy(4-phenylbutyl)phosphinyl]amino]-octahydro-10-oxo-6H-pyridazo[1,2-a][1,2]diazepine-1(S)-carboxylic acid,
methyl 9(S)-[(ethoxy)(5-phenylpentyl)phosphinyl]-octahydro-6,10-dioxo-6H-pyridazo[1,2-a][1,2]diazepine-1(S)-carboxylate,
methyl 9(S)-[(ethoxy)(4-phenylbutyl)phosphinyl]-octahydro-6,10-dioxo-6H-pyridazo[1,2-a][1,2]diazepine-1(S)-carboxylate,
methyl 9(S)-[(ethoxy)(3-phenylpropyl)phosphinyl]-octahydro-6,10-dioxo-6H-pyridazo[1,2-a][1,2]diazepine-1(S)-carboxylate,
methyl 9(S)-[(ethoxy)(phenethyl)phosphinyl]-octahydro-6,10-dioxo-6H-pyridazo[1,2-a][1,2]diazepine-1(S)-carboxylate,
9(S)-[hydroxy(5-phenylpentyl)phosphinyl]-octahydro-6,10-dioxo-6H-pyridazo[1,2-a][1,2]diazepine-1(S)-carboxylic acid,
9(S)-[hydroxy(4-phenylbutyl)phosphinyl]-octahydro-6,10-dioxo-6H-pyridazo[1,2-a][1,2]diazepine-1(S)-carboxylic acid,
9(S)-[hydroxy(3-phenylpropyl)phosphinyl]-octahydro-6,10-dioxo-6H-pyridazo[1,2-a][1,2]diazepine-1(S)-carboxylic acid,
9(S)-[hydroxy(phenethyl)phosphinyl]octahydro-6,10-dioxo-6H-pyridazo[1,2-a][1,2]diazepine-1(S)-carboxylic acid,
methyl 9(S)-[[ethoxy(phenethyl)phosphinyl]methyl]octahydro-6,10-dioxo-6H-pyridazo[1,2-a][1,2]diazepine-1(S)-carboxylate,
9(S)-[[hydroxy(phenethyl)phosphinyl]methyl]octahydro-6,10-dioxo-6H-pyridazo[1,2-a][1,2]diazepine-1(S)-carboxylic acid,
methyl 9(S)-[[ethoxy(phenethyl)phosphinyl]methyl]octahydro-10-oxo-6H-pyridazo[1,2-a][1,2]diazepine-1(S)-carboxylate,
methyl 9(S)-[(ethoxy)(4-phenylbutyl)phosphinyl]-octahydro-10-oxo-6H-pyridazo[1,2-a][1,2]diazepine-1(S)-carboxylate,
ethyl 9(S)-[[(4-benzyloxybutyl)(ethoxy)phosphinyl]methyl]-octahydro-6,10-dioxo-6H-pyridazo[1,2-a][1,2]diazepine-1(S)-carboxylate,
9(S)-[[(4-benzyloxybutyl)(hydroxy)phosphinyl]methyl]-octahydro-6,10-dioxo-6H-pyridazo[1,2-a][1,2]diazepine-1(S)-carboxylic acid,
9(S)-[[(4-hydroxybutyl)(hydroxy)phosphinyl]methyl]-octahydro-6,10-dioxo-6H-pyridazo[1,2-a][1,2]diazepine-1(S)-carboxylic acid,
9(S)-[[(4-aminobutyl)(ethoxy)phosphinyl]methyl]-octahydro-6,10-dioxo-6H-pyridazo[1,2-a][1,2]diazepine-1(S)-carboxylate,
9(S)-[[(4-aminobutyl)(hydroxy)phosphinyl]methyl]-octahydro-6,10-dioxo-6H-pyridazo[1,2-a][1,2]diazepine-1(S)-carboxylic acid,
tert.butyl octahydro-9(S)-[[methoxy(4-nitrophenethyl)phosphinyl]methyl]-6,10-dioxo-6H-pyridazo[1,2-a][1,2]diazepine-1(S)-carboxylate,
octahydro-9(S)-[[methoxy(4-nitrophenethyl)phosphinyl]methyl]-6,10-dioxo-6H-pyridazo[1,2-a][1,2]diazepine-1(S)-carboxylic acid,
octahydro-9(S)-[[hydroxy(4-nitrophenethyl)phosphinyl]methyl]-6,10-dioxo-6H-pyridazo[1,2-a][1,2]diazepine-1(S)-carboxylic acid,
9(S)-[[(4-aminophenethyl)hydroxyphosphinyl]methyl]-octahydro-6,10-dioxo-6H-pyridazo[1,2-a][1,2]diazepine-1(S)-carboxylic acid,
9(S)-[[(4-aminophenethyl)methoxyphosphinyl]methyl]-octahydro-6,10-dioxo-6H-pyridazo[1,2-a][1,2]diazepine-1(S)-carboxylic acid and
octahydro 9(S)-[[(hydroxy)[4-(1-iminoethylamino)phenethyl]phosphinyl]methyl]-6,10-dioxo-6H-pyridazo[1,2-a][1,2]diazepine-1(S)-carboxylic acid.

19. A compound of the formula

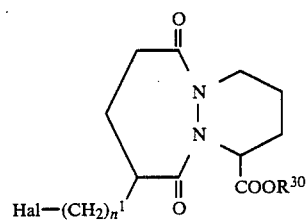

IIa wherein $R^{30}$ is alkyl or aralkyl; Hal is halogen; and $n^1$ is 1 or 2,
and racemates, enantiomers or diastereoisomers thereof.

20. A compound of the formula

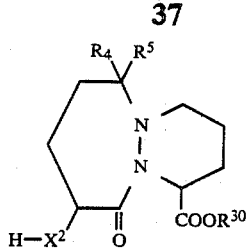
IVa
wherein $R^4$ and $R^5$ each are hydrogen or $R^4$ and $R^5$ together are oxo; $R^{30}$ is alkyl or aralkyl; and $X^2$ is oxygen or $-NR^{61}-$ in which $R^{61}$ is alkyl or aralkyl, and racemates, enantiomers or diastereoisomers thereof.
21. The compound of claim 20, wherein $X^2$ is oxygen.
* * * * *